(12) United States Patent
Nicholas et al.

(10) Patent No.: US 10,888,851 B2
(45) Date of Patent: Jan. 12, 2021

(54) HYDROCARBON CONVERSION USING UZM-50

(71) Applicant: UOP LLC, Des Plaines, IL (US)

(72) Inventors: Christopher P. Nicholas, Evanston, IL (US); Mark A. Miller, Niles, IL (US); Melissa M. Galey, Chicago, IL (US); John Mowat, Arlington Heights, IL (US); Collette Nicholas, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 443 days.

(21) Appl. No.: 15/857,458

(22) Filed: Dec. 28, 2017

(65) Prior Publication Data

US 2019/0201881 A1    Jul. 4, 2019

(51) Int. Cl.
| | | |
|---|---|---|
| *C07C 4/06* | (2006.01) | |
| *B01J 29/70* | (2006.01) | |
| *G01N 23/20* | (2018.01) | |
| *C01B 39/02* | (2006.01) | |

(52) U.S. Cl.
CPC ........... *B01J 29/7007* (2013.01); *B01J 29/70* (2013.01); *C01B 39/02* (2013.01); *C07C 4/06* (2013.01); *G01N 23/20075* (2013.01); *B01J 2231/005* (2013.01); *B01J 2231/40* (2013.01); *C01P 2002/72* (2013.01); *C01P 2002/82* (2013.01); *C01P 2004/04* (2013.01); *C07C 2529/06* (2013.01); *C07C 2529/70* (2013.01)

(58) Field of Classification Search
CPC .. C01B 39/48; C01P 2002/72; C01P 2004/14; C01P 2006/14; C01P 2006/17; B01J 29/70; B01J 29/7007; C07C 4/06; C07C 2529/70; C07C 2529/06
See application file for complete search history.

(56) References Cited

PUBLICATIONS

Chen et al, "Beta zeoltie made from mesoporous materials and its hydrocracking performance", Catalysis Today 116 (2006) 2-5 (Year: 2006).*

Yu, Zheng-Bao, et al., Intergrown New Zeolite Beta Polymorphs with Interconnected 12-Ring Channels Solved by Combining Electron Crystallography and Single-Crystal X-Ray Diffraction, Chem. Mater. 2012, 24, 3701-3706.

(Continued)

*Primary Examiner* — David M Brunsman

(57) ABSTRACT

A new aluminosilicate zeolite designated UZM-50, methods of making the zeolite, and its use as a catalyst in hydrocarbon conversion processes are described. This zeolite is represented by the empirical formula:

$$M^+{}_m R_r Al_{1-x} E_x Si_y O_z$$

where M is selected from the group consisting of hydrogen, sodium, potassium, magnesium, calcium or combinations thereof, R is the organic structure directing agent or agents derived from reactants R1 and R2 where R1 is an amine essentially incapable of undergoing pyramidal inversion and having 7 or fewer carbon atoms, and R2 is a dihaloalkane, and E is an element selected from the group consisting of gallium, iron, boron and mixtures thereof. UZM-50 has utility in various hydrocarbon conversion reactions such as conversion of an aromatic molecule to another aromatic molecule.

16 Claims, 8 Drawing Sheets

(56) References Cited

PUBLICATIONS

Larlus, Olivier, et al., A Powerful Structure-Directing Agent for the Synthesis of Nanosized Al- and High Silica Zeolite Beta in Alkaline Medium, Microporous and Mesoporous Materials 142 (2011) 17-25, 2010.

Kuechl, Dorothy, et al., Multiple Paths to Nanocyrstalline High Silica Beta Zeolite, Microporous and Mesoporous Materials 127 (2010) 104-118.

Corma, Avelino, et al., Synthesis and Structure of Polymorph B of Zeolite Beta, Chem. Matter, 2008, 20 (9), 3218-3223.

Moliner, Manuel, et al., Synthesis of the Ti-Silicate Form of BEC Polymorph of β-Zeolite Assisted by Molecular Modeling, J. Phys. Chem. C, 2008, 112 (49), 19547-19554.

Kobler, Johannes, et al., High-Silica Zeoliteβ: From Stable Colloidal Suspensions to Thin Films, J. Phys. Chem. C 2008, 112, 14274-14280.

Ding, Lianhui, et al., Nanocrystalline Zeolite Beta: The Effect of Template Agent on Crystal Size, Materials Research Bulletin 42 (2007), 584-590.

Cantin, Angel, et al., Synthesis and Characterization of the All-Silica Pure Polymorph C and an Enriched Polymorph B Intergrowth of Zeolite Beta, Angew. Chem. Int. Ed., 2006, 45, 8013-8015.

Mihailova, B., et al., Interlayer Stacking Disorder in Zeolite Beta Family: A Raman Spectroscopic Study, Phys. Chem. Chem. Phys., 2005, 7, 2756-2763.

Takewaki, Takahiko, et al., Zincosilicate CIT-6: A Precursor to a Family of *BEA-Type Molecular Sieves, J. Phys. Chem. B 1999, 103, 2674-2679.

Szostak, Rosemarie, et al., High-Resolution TEM Imaging of Extreme Faulting in Natural Zeolite Tschernichite, J. Phys. Chem. 1995, 99, 2104-2109.

Smith, Joseph V., et al., Tschernichite, the Mineral Analogue of Zeolite Beta, J. Chem. Soc., Chem. Commun., 1991.

Higgins, J.B., et al., The Framework Topology of Zeolite Beta, Zeolites, 1988, vol. 8, Nov. 446-452.

Perez-Pariente, Joaquin, et al, Crystallization Mechanism of Zeolite Beta from (TEA)2O, NA2O, and K2O Containing Aluminosilicate Gels, Applied Catalysis, 31 (1987) 35-64.

Carpenter, John R., et al., Further Investigations on Constraint Index Testing of Zeolites That Contain Cages, Journal of Catalysis 269 (2010) 64-70.

V.J. Frillette, et al., Catalysis by Crystalline Aluminosilicates: Characterization of Intermediate Por-Size Zeolites by the "Constraint Index", Journal of Catalysis 67, 218-222 (1981).

S.I. Jones, et al., The Constraint Index Test Revisited: Anomalies Based Upon New Zeolite Structure Types, Microporous and Mesoporous Materials 35-36 (2000) 31-46.

* cited by examiner

HYDROCARBON CONVERSION USING UZM-50

This invention relates to a new aluminosilicate zeolite designated UZM-50 and its use as a catalyst in hydrocarbon conversion processes. This zeolite is represented by the empirical formula:

$$M^+{}_mR_rAl_{1-x}E_xSi_yO_z$$

where M is selected from the group consisting of hydrogen, sodium, potassium, magnesium, calcium or combinations thereof, R is the organic structure directing agent or agents derived from reactants R1 and R2 where R1 is an amine essentially incapable of undergoing pyramidal inversion and having 7 or fewer carbon atoms, and R2 is a dihaloalkane, and E is an element selected from the group consisting of gallium, iron, boron and mixtures thereof. UZM-50 has utility in various hydrocarbon conversion reactions such as conversion of an aromatic molecule to another aromatic molecule.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

As used herein, zeolites may be referred to by improper name, such as beta, proper name, such as CIT-6, or by structure type code, such as *BEA. These three letter codes indicate atomic connectivity and hence pore size, shape and connectivity for the various known zeolites. The list of these codes may be found in the Atlas of Zeolite Framework Types, which is maintained by the International Zeolite Association Structure Commission at http://www.iza-structure.org/databases/. At present, 234 structure types are known and catalogued by the IZA. One such structure type, *BEA has been described in the literature and is known to contain 3-dimensional 12-ring channels. Zeolites are distinguished from each other on the basis of their composition, crystal structure, and adsorption properties. One method commonly used in the art to distinguish zeolites is x-ray diffraction. A newer x-ray method is small angle x-ray scattering, SAXS.

Beta zeolite was first described structurally in the literature by Higgins, et al. in Zeolites, 1988, 8, 446-52. Using tetraethylammonium as the cationic organic structure directing agent (OSDA), they crystallized a material having a powder x-ray diffraction pattern containing a combination of sharp and broad reflections at $SiO_2/Al_2O_3$ ratios in the range of 30-50. They identified disorder along the [001] direction and proposed three polymorphs of the beta zeolite, A, B, and C. These three polymorphs are constructed from the same layer but with different shifts along the a or b axes. Beta zeolite has at least peaks in the x-ray diffraction pattern at 7.5, 13.44, 21.38, and 22.43°2θ using Cu—Kα radiation.

Corma and coworkers (Chem. Mater. 2008, 20, 3218-23) synthesized materials significantly enriched in polymorph B using 4,4-dimethyl-4-azoniatricyclo[5.2.2.0]undec-8-ene as the OSDA. This material has an x-ray diffraction pattern with peaks at positions of at least 7.5, 8.2, 13.5, 21.4, and 22.4°2θ using Cu—Kα radiation.

Polymorph C has been synthesized by Moliner, et al., using 4,4-dimethyl-4-azoniatricyclo[5.2.2.0]undec-8-ene as the OSDA. This polymorph has been given the structure code BEC. The ITQ-17 material so produced (J. Phys. Chem. C 2008, 112, 19547-54) comprises titanium and has an x-ray diffraction pattern with peaks at positions of at least 6.9, 9.6, 15.3, 19.2, and 22.2°2θ using Cu—Kα radiation.

In addition to the A, B, and C polymorphs, two additional polymorphs of the beta zeolite system have been synthesized and named SU-78A and SU-78B. Yu, et al., described the SU-78 material synthesized using either N,N-dimethyl-dicyclohexylammonium or N-ethyl-N-methyl-dicyclohexylammonium as the OSDA in Chem. Mater. 2012, 24, 3701-6 as an intergrowth with complex twinning and disorder of the SU-78A and SU-78B polymorphs. These materials comprise germanium and have an x-ray diffraction pattern with at least 9 peaks using Cu—Kα radiation.

Takewaki, et al., discovered the CIT-6 family of materials (J. Phys. Chem. B 1999, 103, 2674-2679) as a composition comprising zinc which can be extracted in various post-synthesis treatments. These materials are of the disordered *BEA type and have an x-ray diffraction pattern with at least 6 peaks using Cu—Kα radiation.

A naturally occurring mineral version of beta zeolite is also known, called tschernichite. Tschernichite usually comprises calcium and has $SiO_2/Al_2O_3$ ratios in the range of 3-8 and a powder x-ray diffraction pattern containing a combination of sharp and broad reflections. The x-ray diffraction pattern comprises peaks at d-spacings of at least approximately 11.6-12, 6.3, 4.21, 4.02, 3.56, and 3.15 Å using Cu—Kα radiation.

Zeolite beta is of the disordered *BEA zeotype and known to be heavily faulted. A typical preparation comprises about 60% polymorph A and 40% polymorph B with typical ratios of the polymorphs varying by 10-20% according to preparation (Cantin, et al., Angew. Chem. Int. Ed. 2006, 45, 8013-15). Materials comprising intergrowths of the A and B polymorphs are included in the partially disordered material code *BEA. Szostak and coworkers show in J. Phys. Chem. 1995, 99, 2104-9 that tschernichite is also an intergrowth of the A and B polymorphs at about the same ratios.

Many materials described in the literature as nanocrystalline beta zeolites are also known. These include materials synthesized by Mihailova, et al., (Phys. Chem. Phys. Chem. 2005, 7, 2756-63), Ding and Zheng (Mater. Res. Bull. 2007, 42, 584-90), Casci and coworkers (NU-2, Stud. Surf. Sci. Catal. 1989, 49A, 151-160), Perez-Pariente, et al., (Appl. Catal. 1987, 31, 35-64), Kobler, et al., (J. Phys. Chem. C 2008, 112, 14274-80), Larlus, et al., (Micro. Meso. Mater. 2011, 142, 17-25) and Keuchl, et al., (Micro. Meso. Mater. 2010, 127, 104-18). Numerous other zeolites, including other zeolites of the *BEA type, are known.

SUMMARY OF THE INVENTION

A new aluminosilicate zeolite designated UZM-50 has been synthesized. The present invention relates to zeolite UZM-50, a process of making it, and its use as a catalyst in hydrocarbon conversion processes. This microporous crystalline zeolite has a three-dimensional framework of at least $AlO_2$ and $SiO_2$ tetrahedral units and a composition in an as synthesized and anhydrous basis expressed by an empirical formula of:

$$M^+{}_m R_r Al_{1-x} E_x Si_y O_z$$

where M is selected from the group consisting of hydrogen, sodium, potassium, magnesium, calcium and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of nitrogen from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4 \cdot y)/2$. The UZM-50 may be characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table A:

TABLE A

| 2θ | d (Å) | I/I₀ % |
|---|---|---|
| ~7.5 | 11.5-11.9 | S |
| ~22.4 | 3.92-3.99 | VS |

It may be present in the catalyst as unmodified zeolite UZM-50 or as UZM-50 modified zeolite. The UZM-50 containing catalyst may take one of several forms, including for example, a spherical oil-dropped catalyst or an extruded catalyst.

This microporous crystalline UZM-50 zeolite has a three-dimensional framework of at least $AlO_2$ and $SiO_2$ tetrahedral units and a composition in an after calcination and on an anhydrous basis expressed by an empirical formula of:

$$M1^+{}_{m1} Al_{1-x} E_x Si_y O_z$$

where M1 is selected from the group consisting of hydrogen, sodium, potassium, magnesium, calcium, ammonium, hydrogen, and combinations thereof, "m1" is the mole ratio of M to (Al+E) and varies from 0 to about 1, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4 \cdot y)/2$. UZM-50 may be characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table B:

TABLE B

| 2θ | d (Å) | I/I₀ % |
|---|---|---|
| ~7.5 | 11.5-11.9 | VS |
| ~22.4 | 3.93-3.98 | VS |

Another aspect of the invention is a process of making the zeolite. The method comprises forming a reaction mixture including reactive sources of Al, Si, and R, optionally M and E, and heating the reaction mixture to form the zeolite. In a preferred aspect, the reactive source of R is a solution comprising an organoammonium product. In some embodiments, the solution comprising the organoammonium product may be formed by the method comprising (a) preparing an aqueous mixture comprising water, a substituted hydrocarbon, and an amine other than trimethylamine wherein the amine is a tertiary amine having 7 or less carbon atoms and being essentially incapable of undergoing pyramidal inversion, or combinations thereof; (b) reacting the aqueous mixture; and (c) obtaining a solution comprising an organoammonium product.

Yet another aspect of the invention is a hydrocarbon conversion process using the zeolite of the present invention. The process comprises contacting the hydrocarbon with the zeolite at conversion conditions to give a converted hydrocarbon product. The hydrocarbon conversion processes may comprise oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

DETAILED DESCRIPTION OF THE INVENTION

Figure 1:
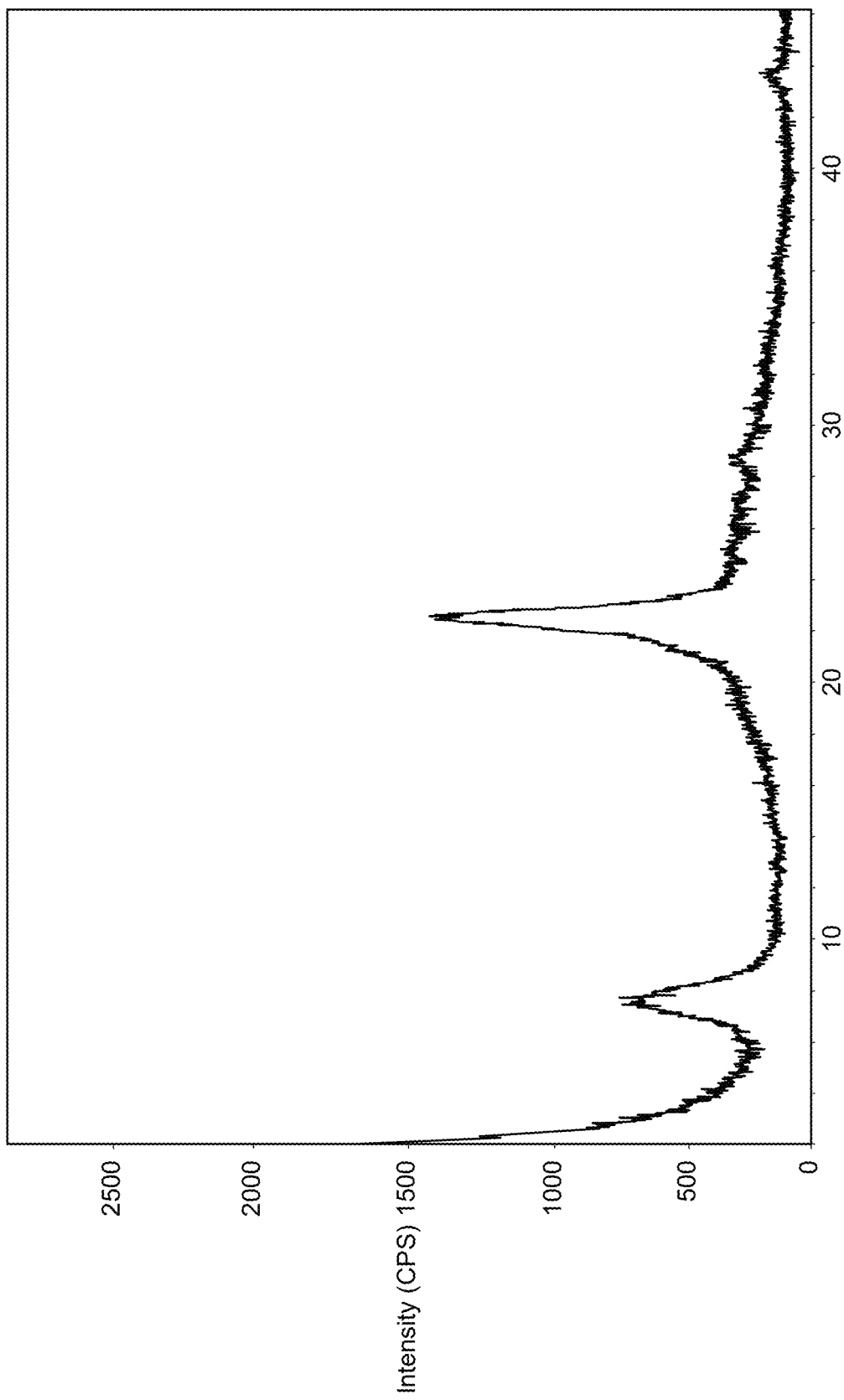
FIG. 1 is an XRD pattern of the UZM-50 zeolite formed in Example 7. This pattern shows the UZM-50 zeolite in the as-synthesized form.

Applicants have prepared a new aluminosilicate zeolite designated as UZM-50. As will be shown in detail, UZM-50 is different from known zeolites in a number of its characteristics, and it finds utility as a catalyst in hydrocarbon conversion processes. The UZM-50 materials are differentiable from other known zeolites, possessing different x-ray diffraction patterns, elemental compositions, Na micropore volumes, Na mesopore volumes, SAXS features, crystallite sizes, IR or Raman spectroscopic signatures, $H_2O$ adsorption capacities, or combinations thereof.

UZM-50 is a microporous crystalline zeolite having a three-dimensional framework of at least $AlO_2$ and $SiO_2$ tetrahedral units and a composition in an as synthesized and anhydrous basis expressed by an empirical formula of:

$$M^+_m R_r Al_{1-x} E_x Si_y O_z$$

where M is selected from the group consisting of hydrogen, sodium, potassium, magnesium, calcium and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of nitrogen from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4 \cdot y)/2$. UZM-50 may be characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table A:

TABLE A

| 2θ | d (Å) | I/I$_0$ % |
|---|---|---|
| ~7.5 | 11.5-11.9 | S |
| ~22.4 | 3.92-3.99 | VS |

In an aspect, M is selected from the group consisting of hydrogen, sodium, potassium, and combinations thereof.

In an aspect, m is greater than about 0.05, or is greater than about 0.1, or is less than about 0.5, or is less than about 0.4. In an aspect, x is greater than about 0.05, or is less than about 0.75, or is less than about 0.5, or is less than about 0.4. In an aspect, y is greater than about 6, or is greater than about 7, or is greater than about 8, or is less than about 50, or is less than about 40, or is less than about 30.

R is the organic structure directing agent or agents derived from reactants R1 and R2 where R1 is at least one neutral monoamine having 7 or fewer carbon atoms and R2 is a dihalogen substituted alkane having between 3 and 6 carbon atoms. In an aspect, r is greater than about 0.25, or is greater than about 0.3, or is less than about 3, or is less than about 2.5.

In an aspect, the substituted alkane R2 is a dihalogen substituted alkane having from 3 to 6 carbon atoms selected from the group consisting of 1,2-di-halo-propane, 1,3-di-halo-butane, 1,3-di-halo-pentane, 1,4-di-halo-pentane, 2,4-di-halo-pentane, 1,5-di-halo-hexane, 1,4-di-halo-hexane, 1,3-di-halo-hexane, 2,4-di-halo-hexane, and 2,5-di-halo-hexane. In an aspect, R2 has 5 or 6 carbon atoms.

R2 may be an A,Ω-dihalogen substituted alkane having between 3 and 6 carbon atoms selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof.

R1 comprises at least one tertiary monoamine being essentially incapable of undergoing pyramidal inversion and having 7 or fewer carbon atoms. R1 may comprise combinations of multiple neutral monoamines having 7 or fewer carbon atoms.

Suitable amines include those for which at least one conformer is essentially incapable of undergoing pyramidal inversion. The IUPAC definition of pyramidal inversion is given as, "a polytopal rearrangement in which the change in bond directions to a three-coordinate central atom having a pyramidal arrangement of bonds (tripodal arrangement) causes the central atom (apex of the pyramid) to appear to move to an equivalent position on the other side of the base of the pyramid. If the three ligands to the central atom are different pyramidal inversion interconverts enantiomers." The tripodal nature of many nitrogen compounds results in the ability of these compounds to undergo pyramidal inversion. Typically, the energy barrier to inversion is low for unconstrained molecules. For example, ammonia ($NH_3$) has an inversion barrier of 24.5 kJ mol$^{-1}$, with an observed inversion frequency of about $2.4*10^{10}$ s$^{-1}$, dimethylamine has an inversion barrier of 18 kJ mol$^{-1}$, triisopropylamine has an inversion barrier of 6-8 kJ mol$^{-1}$ and dimethylethylamine has an inversion barrier of 22 kJ mol$^{-1}$. However, inversion barrier energy can become very high when the nitrogen substituents are part of a small ring or other rigid molecule as in the case of 1-methylpyrrolidine. Molecules defined as essentially incapable of undergoing pyramidal inversion have an inversion barrier energy of at least about 28 kJ mol$^{-1}$, or at least about 30 kJ mol$^{-1}$. A discussion of pyramidal inversion may be found in Rauk, A., et al., (1970), Pyramidal Inversion. Angew. Chem. Int. Ed. Engl., 9: 400-414, with further discussion specifically for amines found in "Inorganic Chemistry" edited by Arnold F. Holleman, et al., Academic Press, 2001. Molecules may exist in many conformers or folding patterns. For example, it is well known that both chair and boat forms of cyclohexane exist and interconvert between the two different conformers. In an aspect of the invention, at least one conformer of the amine is essentially incapable of undergoing pyramidal inversion.

Table 1 provides examples of molecules essentially incapable of undergoing pyramidal inversion.

TABLE 1

| Molecule Name | Inversion Barrier (kJ mol$^{-1}$) |
|---|---|
| N-methylhomopiperidine | 28-29 |
| 1-methyl-4-piperidone | 30.7 |
| trimethylamine | 31-35 |
| 1,3,3-trimethylpyrrolidine | 31 |
| N-methylpyrrolidine | 31-35 |
| 3-methyl-1-thia-3-azacyclopentane | 33 |
| 9-methyl-9-azabicyclo[3.3.1]nonane | 34 |
| N-methyl piperidine (equatorial) | 36.4 |
| 1,2,2,6-tetramethylpiperidine (axial) | 38 |
| 2-methyl-dihydro-2-azaphenalene | 40.5 |
| methylazetidine | 42 |
| 1,2,2,6-tetramethylpiperidine (equitorial) | 46 |
| 4-methyl-1-oxa-4-azacyclohexane | 48 |
| 2-methyl-1-oxa-2-azacyclohexane (equitorial) | 57 |
| 2-methyl-1-oxa-2-azacyclopentane | 65 |
| methylaziridine | 80-90 |

In an aspect, R1 may be selected from the group consisting of 1-methylaziridine, 1-ethylpyrrolidine, 1-methylpyrrolidine, 1-ethylazetidine, 1-methylazetidine, 1-methyl homopiperidine, 1-(2-hydroxyethyl)pyrrolidine, diethylmethylamine, dimethylethylamine, dimethylbutylamine, dimethylpropylamine, dimethylisopropylamine, methylethylpropylamine, methylethylisopropylamine, 1-methyl-4-piperidone, 1,3,3-trimethylpyrrolidine, 3-methyl-1-thia-3-azacyclopentane, 1-methylpiperidine, 1,2,2,6-tetramethylpiperidine, 9-methyl-9-azabicyclo[3.3.1]nonane, 1-methyloctahydro-1H-cyclopenta[B]pyridine, 4-methyl-1-oxa-4-azacyclohexane, 4-ethyl-1-oxa-4-azacyclohexane, 1-alkylpyrrolidines, 1-alkylpiperidines, and 4-alkylmorpholines, and combinations thereof.

1-alkylpyrrolidines may include 1-methylpyrrolidine, 1-ethylpyrrolidine, 1-propylpyrrolidine, and 1-isopropylpyrrolidine. 1-alkylpiperidines may include 1-methylpiperidine, 1,2-dimethylpiperidine, 1,3-dimethylpiperidine, 1,4-dimethylpiperidine and 1-ethylpiperidine. 4-alkylmorpholines may include 4-methylmorpholine, 4-ethylmorpholine, 2,4-dimethylmorpholine, and 3,4-dimethylmorpholine.

In an aspect, the tertiary amine R1 having 7 or fewer carbon atoms and being essentially incapable of undergoing pyramidal inversion is selected from the group consisting of 1-alkylpyrrolidines, 1-alkylpiperidines, 4-alkylmorpholines, and combinations thereof.

Pyrrolidine is a 5-membered heterocycle with an N atom; 1-alkylpyrrolidines include 1-alkylpyrrolidine, 1-alkyl-2-alkylpyrrolidine, 1-alkyl-3-alkyl-pyrrolidine, 1-alkyl-2-alkyl-2-alkylpyrrolidine, 1-alkyl-2-alkyl-3-alkylpyrrolidine, 1-alkyl-2-alkyl-4-alkylpyrrolidine, 1-alkyl-2-alkyl-5-alkylpyrrolidine, 1-alkyl-3-alkyl-3-alkylpyrrolidine, 1-alkyl-3-alkyl-4-alkylpyrrolidine, 1-alkyl-3-alkyl-5-alkylpyrrolidine, and 1-alkyl-4-alkyl-4-alkylpyrrolidine where alkyl has the formula $C_nH_{2n+1}$ and n is in the range from 1 to 3.

Piperidine is a 6-membered heterocycle with an N atom; 1-alkylpiperidines include 1-alkyl piperidine, 1-alkyl-2-alkyl piperidine, 1-alkyl-3-alkyl-piperidine, 1-alkyl-4-alkyl-piperidine, 1-alkyl-2-alkyl-2-alkyl piperidine, 1-alkyl-2-alkyl-3-alkyl piperidine, 1-alkyl-2-alkyl-4-alkyl piperidine, 1-alkyl-2-alkyl-5-alkyl piperidine, 1-alkyl-2-alkyl-6-alkyl piperidine, 1-alkyl-3-alkyl-3-alkyl piperidine, 1-alkyl-3-alkyl-4-alkyl piperidine, 1-alkyl-3-alkyl-5-alkyl piperidine, 1-alkyl-3-alkyl-6-alkyl piperidine, and 1-alkyl-4-alkyl-4-alkyl piperidine where alkyl has the formula $C_nH_{2n+1}$ and n is in the range from 1 to 2.

Morpholine is a 6-membered heterocycle with an N atom and an O atom; 4-alkylmorpholines include 4-alkyl morpholine, 4-alkyl-2-alkyl morpholine, 4-alkyl-3-alkyl-morpholine, 4-alkyl-2-alkyl-2-alkyl morpholine, 4-alkyl-2-alkyl-3-alkyl morpholine, 4-alkyl-2-alkyl-5-alkyl morpholine, 4-alkyl-2-alkyl-6-alkyl morpholine, 4-alkyl-3-alkyl-3-alkyl morpholine, 4-alkyl-3-alkyl-5-alkyl morpholine, and 4-alkyl-3-alkyl-6-alkyl morpholine, where alkyl has the formula $C_nH_{2n+1}$ and n is in the range from 1 to 3. Alkyl groups in the previous classes can be the same, different or any combination thereof at the different carbon atoms at which they are substituted.

In an aspect, the mole ratio of the amine to the substitution is from about 1:1 to about 2:1, or from about 1:1 to about 1.5:1. Typically, the mole ratio of amine to substitution may be approximately 1. Thus, when 1,5-dibromopentane is used as the substituted hydrocarbon, approximately 2 equivalents of amine R1 may be used per equivalent of dibromopentane R2.

The UZM-50 material may be synthesized from a reaction mixture having a composition expressed in terms of mole ratios of the oxides of:

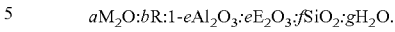

$$aM_2O:bR:1-eAl_2O_3:eE_2O_3:fSiO_2:gH_2O.$$

where M is selected from the group consisting of hydrogen, sodium, potassium, magnesium, calcium or combinations thereof, "a" has a value from 0 to about 3, "b" is the mole ratio of nitrogen from the organic structure directing agent or agents R to (Al+E) and has a value from about 0.05 to about 12, R is derived from R1 and R2, E is an element selected from the group consisting of gallium, iron, boron, and mixtures thereof, "e" has a value from 0 to about 1.0, "f" has a value from greater than 9 to about 60 and "g" has a value from about 200 to about 2000. In an embodiment, "b" may be greater than 0.5 or greater than about 1, or greater than about 2, or greater than about 3, or greater than about 4, or greater than about 5, or less than about 12, or less than about 10, or less than about 9, or less than about 8, or less than about 7, or combinations thereof. In an embodiment, "e" may be less than 1, or less than 0.50, or less than 0.40. In an embodiment, "f" may be greater than about 15, or greater than about 30, or greater than about 40, or less than about 50, or less than about 40, or less than about 30. In an embodiment, "g" may be greater than about 200, or greater than about 300, or greater than about 400, or less than about 1500, or less than about 1000, or less than about 500. The process may further comprise adding UZM-50 seeds to the reaction mixture. In an aspect, M may be selected from the group consisting of sodium, potassium, magnesium, calcium or combinations thereof.

Sources of M include, but are not limited to, sodium hydroxide, potassium hydroxide, sodium aluminate, potassium aluminate, sodium silicate, and potassium silicate. The sources of E include, but are not limited to, alkali borates, boric acid, precipitated gallium oxyhydroxide, gallium sulfate, ferric sulfate, ferric chloride and mixtures thereof. The sources of aluminum include, but are not limited to, aluminum alkoxides, precipitated aluminas, aluminum metal, aluminum hydroxide, sodium aluminate, potassium aluminate, aluminum salts and alumina sols. Specific examples of aluminum alkoxides include, but are not limited to, aluminum sec-butoxide and aluminum ortho isopropoxide. Sources of silica include, but are not limited to, tetraethylorthosilicate (an alkoxide), colloidal silica, fumed silica, precipitated silica and alkali silicates. If alkoxides are used, it is preferred to include a distillation or evaporative step to remove the alcohol hydrolysis products.

This invention relates to a process for preparing crystalline aluminosilicate UZM-50 compositions including quaternary ammonium salts. Preferentially, the process comprises a process for preparing quaternary ammonium salts. The process may involve first forming an aqueous phase solution of a quaternary ammonium salt from suitable reagents such as a di-substituted alkane and an amine. The pre-reacted quaternary ammonium salt solution may then be incorporated into a zeolite reaction mixture containing sources of aluminum, silicon, and optionally other reagents, and the resultant mixture reacted at a temperature and for a time to crystallize the aluminosilicate UZM-50 composition. Alternatively, the quaternary ammonium salts may be synthesized by other methods known in the art and incorporated into the reaction mixture.

In one aspect, the invention provides a method for synthesizing a zeolite. The method comprises first forming a reaction mixture including reactive sources of Al, Si, R, optionally M and/or E, and then heating the reaction mixture to form the zeolite.

The reaction mixture may be heated at a temperature of about 125° C. to about 185° C. for a time of about 1 day to about 3 weeks in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. The reaction mixture may be heated at a temperature of about 135° C. to about 175° C. for a time of about 1 day to about 3 weeks. In an embodiment, the reaction mixture is heated at a temperature of about 165° C. to about 175° C. for a time of about 1 day to about 1 week. Prior to the heating step, an aging step may be performed at a temperature of about 85° C. to about 125° C. for a time of about 4 hours to about 5 days in a sealed reaction vessel under autogenous pressure.

In some embodiments, the reactive source of R is a solution comprising an organoammonium product formed by the method comprising: (a) preparing an aqueous mixture comprising water, a substituted hydrocarbon, and an amine other than trimethylamine wherein the amine is a tertiary amine having 7 or less carbon atoms and being essentially incapable of undergoing pyramidal inversion, or combinations thereof; (b) reacting the aqueous mixture; and (c) obtaining a solution comprising an organoammonium product. In one version of the method, the step of reacting the aqueous mixture occurs at a temperature between 20° C. and 100° C. In another version of the method, the organoammonium product comprises a structure directing agent R.

In an aspect, R may comprise 1,5-bismethylpyrrolidinium pentane dihydroxide, or 1,5-bisethylpyrrolidinium pentane dihydroxide, or 1,5-bismethylpiperidinium pentane dihydroxide, or 1,5-bisethylpiperidinium pentane dihydroxide, or 1,5-bismethylmorpholinium pentane dihydroxide, or 1,5-bisethylmorpholinium pentane dihydroxide. R may comprise 1,4-bismethylpyrrolidinium butane dihydroxide, or 1,4-bisethylpyrrolidinium butane dihydroxide, or 1,4-bismethylpiperidinium butane dihydroxide, or 1,4-bisethylpiperidinium butane dihydroxide, or 1,4-bismethylmorpholinium butane dihydroxide, or 1,4-bisethylmorpholinium butane dihydroxide. R may comprise 1,6-bismethylpyrrolidinium hexane dihydroxide, or 1,6-bisethylpyrrolidinium hexane dihydroxide, or 1,6-bismethylpiperidinium hexane dihydroxide, or 1,6-bisethylpiperidinium hexane dihydroxide, or 1,6-bismethylmorpholinium hexane dihydroxide, or 1,6-bisethylmorpholinium hexane dihydroxide.

UZM-50, in the as-synthesized and anhydrous basis, is characterized by the x-ray diffraction pattern, having at least the d-spacings and relative intensities set forth in Table A below. Additional peaks, particularly those of very weak intensity, may also be present. All peaks of medium or higher intensity present in UZM-50 are represented in Table A. Diffraction patterns herein were obtained using a typical laboratory powder diffractometer, utilizing the $K_\alpha$ line of copper; Cu K alpha. From the position of the diffraction peaks represented by the angle 2 theta, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: weak (W) means less than 12; medium (M) means in the range 12 to 25; strong (S) means in the range 25 to 65; very strong (VS) means more than 65. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular morphological structures or for samples with crystals which are small enough to cause significant broadening of the X-rays. This can also be the case when the equipment or operating conditions used to produce the diffraction pattern differ significantly from those used in the present case.

TABLE A

| 2θ | d (Å) | I/I₀ % |
|---|---|---|
| ~7.5 | 11.5-11.9 | S |
| ~22.4 | 3.92-3.99 | VS |

In an embodiment, the peak at approximately 22.4°2θ is the strongest peak. In an embodiment, two peaks of strong intensity or greater are present. In an embodiment, fewer than 4 peaks of strong intensity or greater are present. In an embodiment, fewer than 3 peaks of strong intensity or greater are present. In an embodiment, only two peaks of very strong intensity are present. In an embodiment, one peak of strong intensity and one peak of very strong intensity are present.

UZM-50 is a microporous crystalline zeolite having a three-dimensional framework of at least $AlO_2$ and $SiO_2$ tetrahedral units and a composition in an after calcination and on an anhydrous basis expressed by an empirical formula of:

$$M1^+{}_{m1}Al_{1-x}E_xSi_yO_z$$

where M1 represents hydrogen, sodium, potassium, magnesium, calcium, ammonium, or combinations thereof, and E is an element selected from the group consisting of gallium, iron, boron and mixtures thereof, and is characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table B:

TABLE B

| 2θ | d (Å) | I/I₀ % |
|---|---|---|
| ~7.5 | 11.5-11.9 | VS |
| ~22.4 | 3.93-3.98 | VS |

The values of m1, x, y, and z are as described above for the as synthesized version (with m1 having the same values as m).

As will be shown in detail in the examples, the UZM-50 material is thermally stable up to a temperature of at least 600° C., and in another embodiment, up to at least 800° C. Also as shown in the examples and in an aspect, the UZM-50 material may have a mesopore volume as a percentage of total pore volume of greater than 88%, or greater than 90%, or greater than 92% as determined by BET analysis using $N_2$. In an aspect, the UZM-50 material may have a mesopore volume as a percentage of total pore volume of less than 100%, or less than 98%, or less than 95% as determined by BET analysis using $N_2$. In an aspect, the UZM-50 may have a micropore volume of greater than about 0.145 mL/g, or greater than about 0.150 mL/g, or greater than about 0.155 mL/g, or less than about 0.200 mL/g, or less than about 0.192 mL/g, or less than about 0.187 mL/g as determined by BET analysis using $N_2$.

As synthesized, the UZM-50 material will contain some exchangeable or charge balancing cations in its pores. These exchangeable cations can be exchanged for other cations, or in the case of organic structure directing agents (SDAs), they can be removed by heating under controlled conditions. It may be possible to remove some organic SDAs from the UZM-50 zeolite directly by ion exchange. The UZM-50 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination and on an anhydrous basis, the microporous crystalline zeolite UZM-50 displays the XRD pattern shown in Table B. Those peaks characteristic of UZM-50 are shown in Table B. Additional peaks, particularly those of very weak intensity, may also be present. All peaks of medium or higher intensity present in UZM-50 are represented in Table B.

TABLE B

| 2θ | d (Å) | I/I₀ % |
|---|---|---|
| ~7.5 | 11.5-11.9 | VS |
| ~22.4 | 3.93-3.98 | VS |

In an embodiment, two peaks of strong intensity or greater are present. In an embodiment, fewer than 4 peaks of strong intensity or greater are present. In an embodiment, fewer than 3 peaks of strong intensity or greater are present. In an embodiment, only two peaks of very strong intensity are present.

The characteristic full width at half maximum (FWHM) of the UZM-50 or comparative materials may be determined on the basis of the X-ray diffraction pattern of the material using a linear background. This may be most readily accomplished by peak fitting routines known to one skilled in the art, such as those implemented in JADE software available from MDI, but may also be determined via more manual methods. For UZM-50 materials, the FWHM of Peak 1 is the full width (in terms of 2θ) of the peak at 2θ≈7.5° (±0.5°) at half the maximum height of the peak. For UZM-50 materials, the FWHM of Peak 2 is the full width (in terms of 2θ) of the peak at 2θ≈22.4° (±0.5°) at half the maximum height of the peak. The Peak 1 FWHM of UZM-50 may be greater than about 1.25, or may be greater than 1.28, or may be greater than 1.29, or may be greater than 1.30, or may be greater than 1.32. In an aspect, the Peak 1 FWHM of UZM-50 may be less than 2.00, or may be less than 1.75, or may be less than 1.60. The Peak 2 FWHM of UZM-50 may be greater than about 0.80, or may be greater than 0.90, or may be greater than 0.95, or may be greater than 1.00, or may be greater than 1.05. In an aspect, the Peak 2 FWHM of UZM-50 may be less than 2.00, or may be less than 1.75, or may be less than 1.60.

The distance between Peak 1 of UZM-50 and Peak 2 of UZM-50 may be characteristic. An InterPeak distance (in terms of 2θ) may be determined by subtracting the degrees 2θ of Peak 1 from that of Peak 2. In an aspect, the InterPeak distance of UZM-50 (using copper source of wavelength: 1.5418 angstroms) may be greater than 14.75°2θ, or may be greater than 14.78, or may be greater than 14.80, or may be greater than 14.85. In an aspect, the InterPeak distance of UZM-50 may be less than 15.25, or may be less than 15.20, or may be less than 15.15. Table 2 shows characteristics of UZM-50 example materials determined by XRD analysis.

TABLE 2

| Example | Height % Peak 1 | Height % Peak 2 | FWHM Peak 1 | FWHM Peak 2 | InterPeak Distance |
|---|---|---|---|---|---|
| 7, as-synthesized | 38 | 100 | 1.36 | 1.08 | 14.98 |
| 7, calcined | 89 | 100 | 1.38 | 1.15 | 15.03 |
| 7 repeat, calcined | 103.1 | 100 | 1.41 | 1.13 | 15.05 |
| 8, calcined | 82.4 | 100 | 1.39 | 1.14 | 14.88 |
| 9, as-synthesized, 150 C. 13 days | 36.6 | 100 | 1.37 | 1.16 | 14.88 |
| 9, as-synthesized, 160 C. 5 days | 37.3 | 100 | 1.39 | 1.13 | 14.84 |
| 9, as-synthesized, 160 C. 7 days | 39 | 100 | 1.55 | 1.51 | 14.88 |
| 9, as-synthesized, 160 C. 10 days | 40.4 | 100 | 1.36 | 1.09 | 14.86 |
| 9, as-synthesized, 160 C. 13 days | 37.6 | 100 | 1.38 | 1.05 | 14.87 |
| 9, as-synthesized, 175 C. 4 days | 36.1 | 100 | 1.33 | 1.01 | 15.06 |
| 9, as-synthesized, 175 C. 5 days | 40.8 | 100 | 1.43 | 1.51 | 15.03 |
| 9, calcined, 150 C. 13 days | 87.5 | 100 | 1.55 | 1.64 | 14.89 |
| 9, calcined, 160 C. 5 days | 78.4 | 100 | 1.39 | 1.22 | 14.91 |
| 9, calcined, 160 C. 7 days | 86.2 | 100 | 1.37 | 1.18 | 14.97 |
| 9, calcined, 160 C. 10 days | 82.4 | 100 | 1.36 | 1.16 | 14.94 |
| 9, calcined, 160 C. 13 days | 88.3 | 100 | 1.39 | 1.16 | 14.94 |
| 9, calcined, 175 C. 6 days | 69.8 | 100 | 1.34 | 1.10 | 15.11 |
| 11, as-synthesized | 32.7 | 100 | 1.34 | 1.12 | 14.92 |
| 11, calcined | 106.7 | 100 | 1.39 | 1.24 | 14.93 |
| 12A, as-synthesized, 2 days | 36.3 | 100 | 1.37 | 1.10 | 14.90 |
| 12A, as-synthesized, 3 days | 36.2 | 100 | 1.36 | 1.09 | 14.94 |
| 12B, as-synthesized, 2 days | 35.9 | 100 | 1.42 | 1.37 | 14.82 |

TABLE 2-continued

| Example | Height % Peak 1 | Height % Peak 2 | FWHM Peak 1 | FWHM Peak 2 | InterPeak Distance |
|---|---|---|---|---|---|
| 12B, as-synthesized, 3 days | 36.1 | 100 | 1.30 | 1.05 | 14.84 |
| 12A, calcined, 2 days | 81.9 | 100 | 1.39 | 1.18 | 14.93 |
| 12B, calcined, 2 days | 82.1 | 100 | 1.363 | 1.144 | 14.9367 |
| 14, as-synthesized | 35.4 | 100 | 1.41 | 1.08 | 14.89 |
| 14, calcined | 107.7 | 100 | 1.40 | 1.20 | 15.18 |
| 15, calcined 18 h | 90.2 | 100 | 1.48 | 0.98 | 15.29 |
| 16, as-synthesized, 125 C. | 39.9 | 100 | 1.38 | 1.28 | 14.78 |
| 16, as-synthesized, 175 C., 1 day | 34.9 | 100 | 1.41 | 1.16 | 14.91 |
| 16, as-synthesized, 175 C., 2 days | 37.6 | 100 | 1.28 | 1.09 | 14.97 |
| 16, as-synthesized, 175 C., 3 days | 37.8 | 100 | 1.34 | 1.09 | 14.96 |
| 16, calcined, 125 C. | 93.1 | 100 | 1.446 | 1.328 | 14.91 |
| 16, calcined, 175 C., 1 day | 104.9 | 100 | 1.43 | 1.264 | 14.96 |
| 16, calcined, 175 C., 2 days | 92.9 | 100 | 1.393 | 1.201 | 14.99 |
| 16, calcined, 175 C., 3 days | 100 | 100 | 1.385 | 1.191 | 15.01 |
| 17, as-synthesized | 31.5 | 100 | 1.313 | 1.019 | 15.11 |
| 17, calcined | 98.1 | 100 | 1.46 | 1.141 | 15.20 |
| 22, calcined | 109.8 | 100 | 1.363 | 1.3 | 14.92 |
| 25, as-synthesized | 25 | 100 | 1.451 | 1.175 | 14.83 |
| 25, calcined | 125.2 | 100 | 1.369 | 1.445 | 14.95 |
| 33B | 23.2 | 100 | 1.287 | 0.613 | 14.81 |
| 33C | 56.9 | 100 | 1.116 | 0.25 | 14.79 |
| 33D | 46.5 | 100 | 1.282 | 0.508 | 14.85 |

For the determination of the X-ray diffraction pattern, a standard powder diffractometer (e.g., Rigaku Ultima IV) equipped with a graphite monochromator may be used. One skilled in the art understands the basic method of utilizing powder XRD to obtain a diffraction pattern. The measurement conditions may, e.g., be chosen as follows: X-ray generator settings: 40 kV and 44 mA; wavelength: 1.5418 angstroms; divergence and anti-scatter slits: 2/3°; detector slit: 0.3 mm; step size: 0.02 (° 2θ); time/step: 1 seconds.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-50 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species. The separation process may comprise contacting at least two components with the UZM-50 zeolite material to generate at least one separated component.

The UZM-50 zeolite of this invention can also be used as a catalyst or catalyst support in various hydrocarbon conversion processes. The catalyst may contain from about 0 wt % to about 100 wt % of the UZM-50 zeolite, or about 10 wt % to about 100 wt %, or about 20 wt % to about 100 wt %, or about 30 wt % to about 100 wt %, or about 40 wt % to about 100 wt %, or about 50 wt % to about 100 wt %, or about 60 wt % to about 100 wt %, or about 70 wt % to about 100 wt %, or about 80 wt % to about 100 wt %, or about 90 wt % to about 100 wt %, or about 0 wt % to about 90 wt %, or about 0 wt % to about 80 wt %, or about 0 wt % to about 70 wt %, or about 0 wt % to about 60 wt %, or about 0 wt % to about 50 wt %, or about 0 wt % to about 40 wt %, or about 0 wt % to about 30 wt %, or about 0 wt % to about 20 wt %, or about 0 wt % to about 10 wt %.

Hydrocarbon conversion processes are well known in the art and include oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

Using a UZM-50 catalyst composition which contains a hydrogenation promoter such as platinum or palladium, heavy petroleum residual stocks, cyclic stocks and other hydrocrackable charge stocks may be hydrocracked at temperatures in the range of about 204° C. to about 649° C. (400° to 1200° F.) or about 316° C. to about 510° C. (600° F. and 950° F.). Nickel, cobalt, molybdenum and tungsten are additionally known in the art as hydrogenation promoters.

Reaction pressures are in the range of atmospheric to about 24,132 kPa g (3,500 psig), or between about 1379 to about 20,685 kPa g (200 to 3000 psig). Contact times usually correspond to liquid hourly space velocities (LHSV) in the range of about 0.1 $hr^{-1}$ to 15 $hr^{-1}$, or between about 0.2 and 10 $hr^{-1}$. Hydrogen circulation rates are in the range of 178 to about 8,888 std. $m^3/m^3$ (1,000 to 50,000 standard cubic feet (scf) per barrel of charge), or about 355 to about 5,333 std. $m^3/m^3$ (about 2,000 to about 30,000 scf per barrel of charge). Suitable hydrotreating conditions are generally within the broad ranges of hydrocracking conditions set out above.

These same catalysts, i.e. those containing hydrogenation promoters, may also be useful in hydroisomerization processes in which feedstocks such as normal paraffins are converted to saturated branched chain isomers. Hydroisomerization is carried out at a temperature of from about 93° C. to about 450° C. (200° F. to 842° F.), or about 150° C. to about 300° C. (300° F. to 572° F.) with an LHSV value of from about 0.2 to 1.0. Hydrogen is supplied to the reactor in admixture with the hydrocarbon feedstock in molar proportions (H$_2$/HC) of between 1 and 5.

Catalytic cracking processes may be preferably carried out with the UZM-50 composition using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Alkylation of aromatics usually involves reacting an aromatic (C$_2$ to C$_{12}$), especially benzene, with a monoolefin to produce a linear alkyl substituted aromatic. The process may be carried out at an aromatic: olefin (e.g., benzene: olefin) ratio of between 1:1 and 30:1, a olefin LHSV of about 0.3 to about 10 hr$^{-1}$, a temperature of about 100° to about 250° C. and pressures of about 1379 kPa g to about 6895 kPa g (about 200 to about 1000 psig). Further details on apparatus may be found in U.S. Pat. No. 4,870,222 which is incorporated by reference.

Alkylation of isoparaffins with olefins to produce alkylates suitable as motor fuel components may be carried out at temperatures of −30° to 40° C., pressures from about atmospheric to about 6,895 kPa (1,000 psig) and a weight hourly space velocity (WHSV) of 0.1 to about 120. Details on paraffin alkylation may be found in U.S. Pat. Nos. 5,157,196 and 5,157,197, which are incorporated by reference.

Isomerization reactions are carried out under conditions identified for the feedstock. Olefins may be preferably isomerized at temperatures of about 150° C. to about 500° C. (302° F.-932° F.), while paraffins, naphthenes and alkyl aromatics are isomerized at temperatures of from about 350° C. to about 550° C. (662° F.-1022° F.). Particularly desirable isomerization reactions contemplated herein include the conversion of n-heptane and/or n-octane to isoheptanes, iso-octanes, butane and iso-butane, methylcyclopentane to cyclohexane, meta-xylene and/or ortho-xylene to paraxylene, 1-butene to 2-butene and/or isobutene, n-hexene to iso-hexene, cyclohexene to methylcyclopentene etc.

Catalyst compositions comprising UZM-50 may be useful for the oligomerization of olefins to longer olefins such as gasoline and distillate range olefins. Light olefins such as ethene, propene, butene and pentenes may be oligomerized to gasoline or distillate range olefins. Liquid phase operation is typically preferred. Operating pressures may include between about 2.1 MPa (300 psia) and about 10.5 MPa (1520 psia), but other pressures are contemplated depending on feed and recycle such that liquid phase is maintained. With liquid oligomerate recycle, lower pressures are often possible to maintain liquid phase. Temperature may be in a range between about 100° C. and about 350° C. or may be between about 180° C. and about 300° C. The weight hourly space velocity may be between about 0.5 and about 10 hr$^{-1}$. Additional conditions for successful operation may be given in U.S. Pat. No. 9,278,893, hereby incorporated by reference.

Catalyst compositions comprising UZM-50 may be useful for the conversion of an aromatic molecule to another aromatic molecule. The conversion of an aromatic molecule may involve reacting an aromatic feed molecule (C$_6$ to C$_{12}$) over a catalyst comprising UZM-50 to form a product comprising another aromatic molecule. The product aromatic molecule may be of the same, higher, or lower molecular weight than the feed aromatic molecule. The process may be carried out at a WHSV of about 0.1 to about 100 hr$^{-1}$, a temperature of about 50° C. to about 750° C. and pressures of about 101 kPa g to about 20265 kPa g (about 1 atm to about 200 atm). In an aspect, the aromatic molecule feed is selected from the group of benzene, toluene, p-xylene, m-xylene, o-xylene, and combinations thereof. In an aspect, the process is carried out at a WHSV of from about 0.1 to about 10 hr$^{-1}$. In an aspect, the process is carried out at a temperature of about 100° C. to about 500° C. In an aspect, the process may be carried out at a pressure of no greater than about 10132 kPa g (100 atm). In an aspect, the aromatic molecule product is selected from the group of benzene, toluene, p-xylene, m-xylene, o-xylene, and combinations thereof.

By about, we mean within 10% of the value, or within 5% of the value, or within 1% of the value.

The invention will now be further illustrated by the following non-limiting examples.

EXAMPLES

Example 1

852.4 g deionized water was weighed into a 2 L Teflon bottle. The bottle was placed into a 4 L beaker, a stir bar was added, and stirring on a magnetic stir plate was started. 489.7 g 1,5 Dibromopentane, 97% was added. Then 362.7 g 1-Methylpyrrolidine, 97% was added. About 1.5 L water (room temperature (RT)) was placed between the bottle and beaker to help disperse any exotherm. This was allowed to mix overnight. 1697 g of yellow solution was recovered.

Example 2

874.8 g deionized water was weighed into a 2 L Teflon bottle. The bottle was placed into a 4 L beaker, a stir bar was added, and stirring on a magnetic stir plate was started. 474.1 g 1,5 dibromopentane (DBP), 97% was added. Then 400.7 g 1-Methylpiperidine, 99% was added. About 1.5 L water (RT) was placed between the bottle and beaker to help disperse any exotherm. This was allowed to mix overnight. There was no visible vortex in the morning, so the stirring was insufficient. A Heidolph high speed mixer was used to stir the mixture all day. This slowly turned into a yellow solution. The mixing was stopped for about 52 hours and was then resumed for a further 8 hours. A yellow solution resulted with some clear unreacted DBP on the bottom which was separated out. Analysis showed the yellow solution to be 49.5% water.

Example 3

1000 g of Example 1 product was loaded into a 3-necked round bottom flask with overhead stirring. 295.4 g Ag$_2$O, 99% was added, and the flask was covered with aluminum foil. It was mixed for 48 hours at room temperature. Glass filters were used to isolate a clear yellow solution. The solution was filtered a few times over the next week or two. Analysis showed this solution to be 65.5% water.

Example 4

1100 g of Example 2 product was loaded into a 3-necked round bottom flask with overhead stirring. 303.6 g Ag$_2$O was added, and the flask was covered with aluminum foil. It was mixed for 48 hours at room temperature. Glass filters were used to isolate a clear yellow solution. The solution was filtered a few times over the next week or two. Analysis showed this solution to be 64.5% water.

Example 5

6.47 g aluminum hydroxide (Pfaltz&Bauer) was stirred into 213.0 g of Example 3 product. When it became a solution, 200 g Ludox AS-40 colloidal silica was added. To this mixture, 196.9 g deionized water was added, and the resulting mixture was placed in a 100° C. oven overnight in a sealed Teflon bottle. In the morning, this was found to be a soft gel. The gel was cooled, and 196.9 g water was added before the mixture was re-slurried for use. ICP (inductively coupled plasma) analysis shows the slurry consists of 4.82% Si and 0.24% Al.

Example 6

6.47 g aluminum hydroxide (Pfaltz&Bauer) was stirred into 228.14 g of Example 4 product. When it became a solution, 200 g Ludox AS-40 was added. To this mixture, 202.6 g deionized water was added, and the resulting mixture was placed in a 100° C. oven overnight in a sealed Teflon bottle. In the morning, this was found to be a soft gel. The gel was cooled, and 202.6 g water added before the mixture was re-slurried for use.

Example 7

Figure 2:
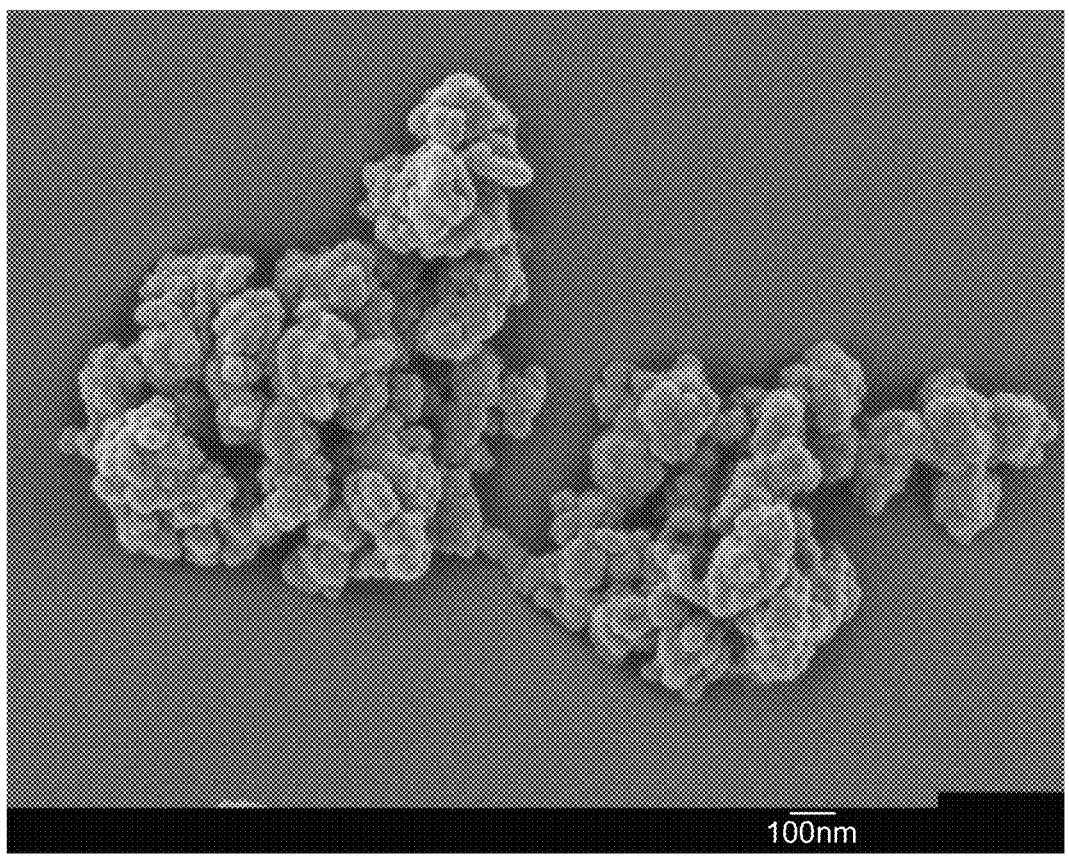
FIG. 2 shows a SEM micrograph of the Example 7 UZM-50 product at 100 nm resolution.
Figure 3:
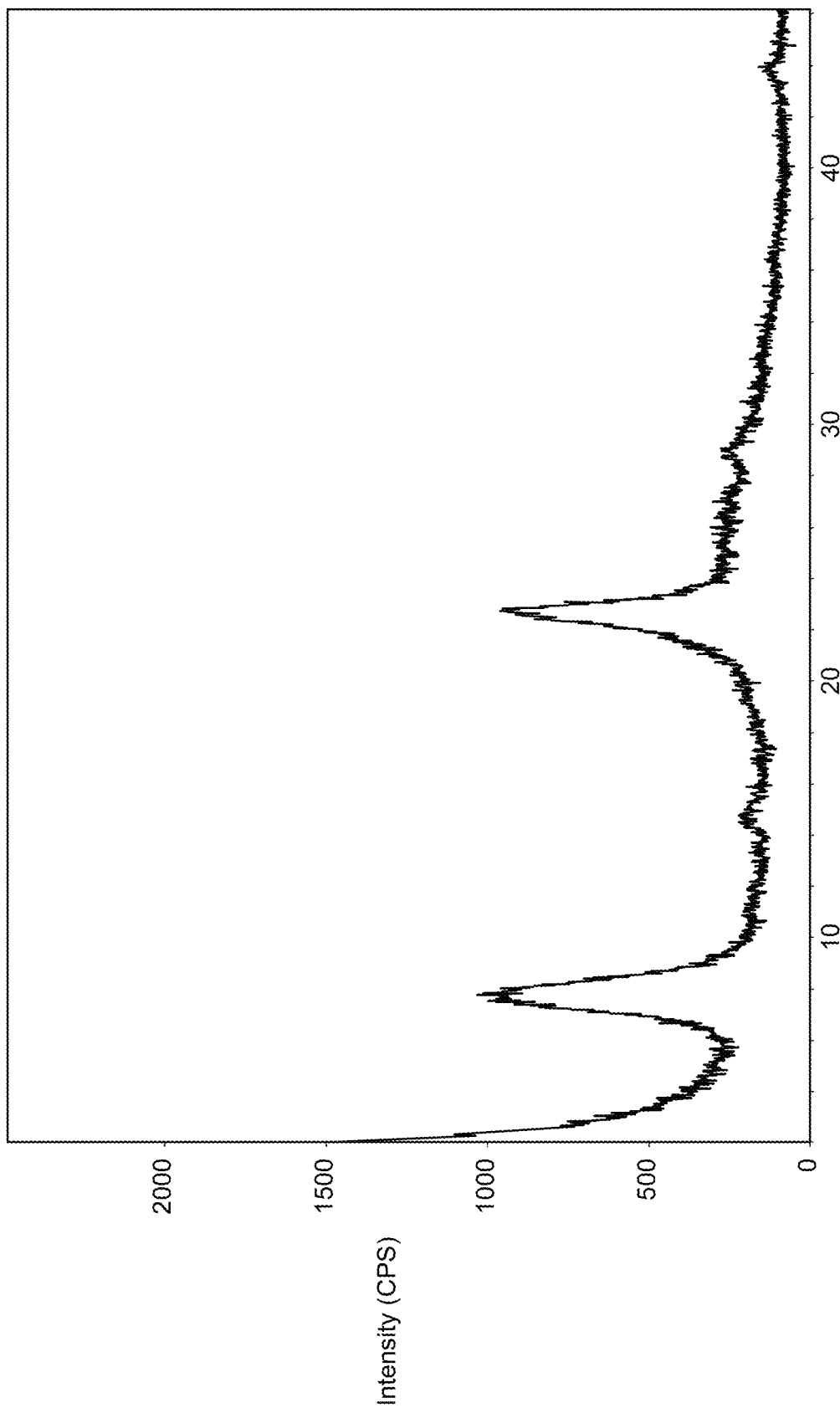
FIG. 3 is also an XRD pattern of the UZM-50 zeolite formed in Example 7. This pattern shows the UZM-50 zeolite after calcination.
Figure 4:
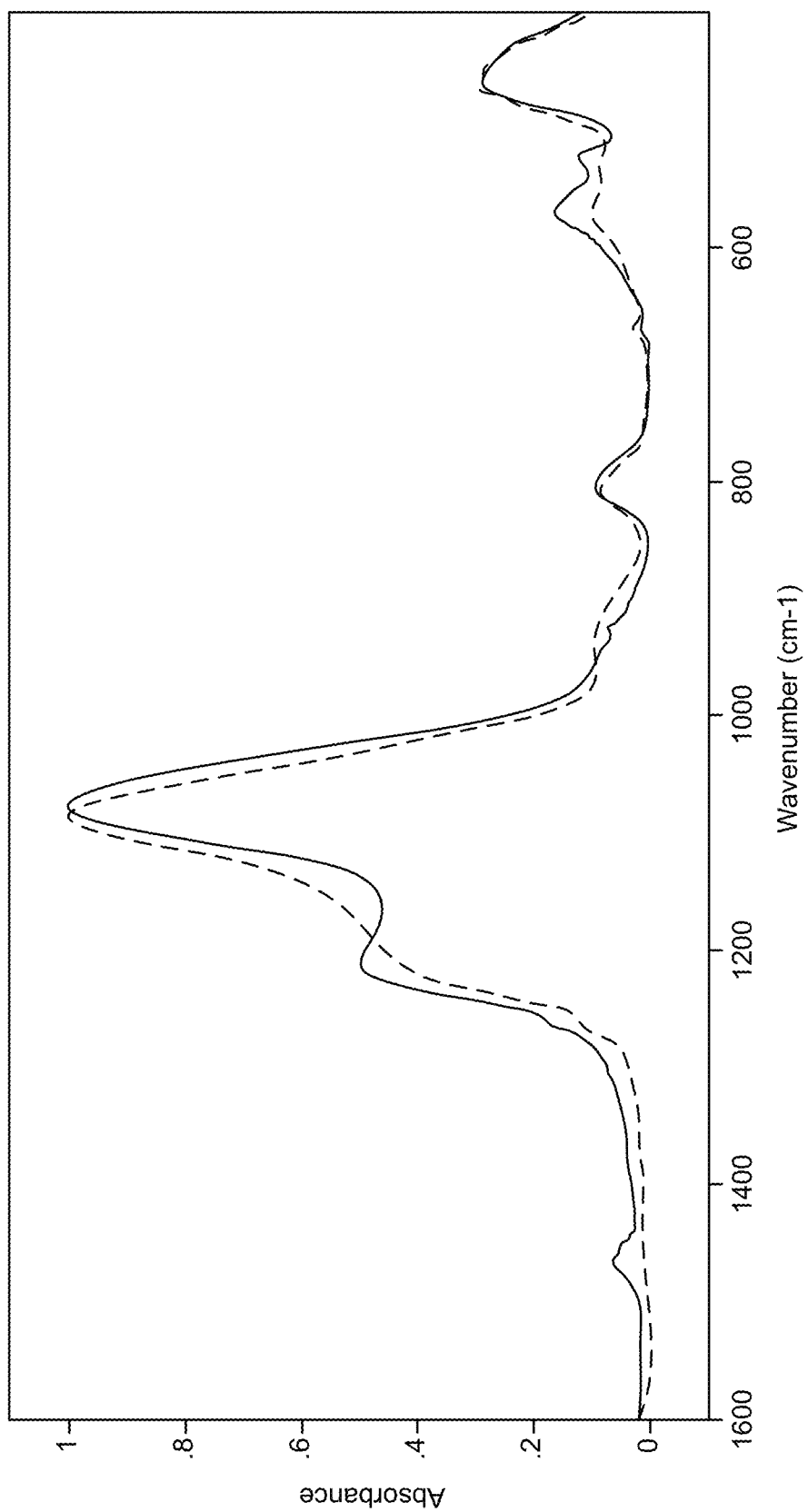
FIG. 4 is an IR spectrum of the UZM-50 zeolite formed in Example 7.

The Example 5 mixture was loaded into 45 cc Parr bombs. Some were digested statically, while others were tumbled. Products made at 160° C. for 13 days for both methods were isolated and identified to be UZM-50 by XRD. The XRD patterns for both methods were very similar. ICP analysis of the static product showed 35.3% Si, 2.07% Al, and 66 ppm Na, therefore a product Si/Al=16.39. The XRD of this as-synthesized material is shown in FIG. 1. The SEM of this as-synthesized material is shown in FIG. 2. This material was then calcined at 600° for 6 hours under flowing air. The XRD of this calcined material is shown in FIG. 3. Analysis showed a $N_2$ BET surface area of 640 $m^2/g$, Langmuir SA of 950 $m^2/g$, total pore volume of 1.241 mL/g, and micropore volume of 0.171 mL/g. IR analysis of the as-synthesized (solid trace) and calcined materials (dashed trace) is shown in FIG. 4. Beta zeolites usually have 4 peaks in the low framework region (Eapen, et. al. Zeolites 1994, 14, 295-302) which are typically around 570-575 $cm^{-1}$, ≠520 $cm^{-1}$ and about 470 and 425 $cm^{-1}$. Table 3 gives frequencies for peaks observed for the as-synthesized material. The frequency of the asymmetric T—O—T shift moves slightly in the calcined material to about 1086.5 $cm^{-1}$.

TABLE 3

| Peak Frequencies, $cm^{-1}$ |
| --- |
| 1465.4 |
| 1209.6 |
| 1075.4 |
| 803.1 |
| 567.3 |
| 521.8 |
| 452.0 |

Example 8

5.86 g NaOH•9.98 $H_2O$ was stirred dropwise into 100 g of Example 5 product. The resulting mixture was equally divided between four 45 cc Parr bombs, put in a rotisserie oven at 160° C., and tumbled at 15 rpm. The resulting products were identified as UZM-50 by XRD. The product from 6 days of synthesis was utilized for analysis by SAXS in Example 32 after calcination and ion-exchange. The product from 9 days of synthesis was sent for analysis, which showed Si/Al=13.54, Na/Al=0.0625, C/N=8.8, and N/Al=1.41.

Example 9

The example 6 mixture was loaded into 45 cc Parr bombs. The product resulting from 150° C. static digestion for 13 days was determined to be UZM-50 by XRD. The products resulting from 160° C. static digestion for 5, 7, and 10 days was determined to be UZM-50 by XRD. The product resulting from 160° C. static digestion for 13 days was determined to be UZM-50 by XRD. This material was calcined at 600° for 6 hours under flowing air. Analysis showed a $N_2$ BET SA of 652 $m^2/g$, Langmuir SA of 971 $m^2/g$, total pore volume of 1.390 mL/g, and micropore volume of 0.173 mL/g. The products resulting from 175° C. static digestion for 4, 5, and 6 days were determined to comprise UZM-50 by XRD.

Example 10

3.50 g NaOH•9.98 $H_2O$ was stirred dropwise into 100 g of Example 6 product. The resulting mixture was equally divided between four 45 cc Parr bombs, put in a rotisserie oven at 160° C., and tumbled at 15 rpm. The resulting products were identified as UZM-50 by XRD. The product obtained after 9 days of synthesis was sent for analysis, which showed Si/Al=15.53, and Na/Al=0.0182.

Example 11

Figure 5:
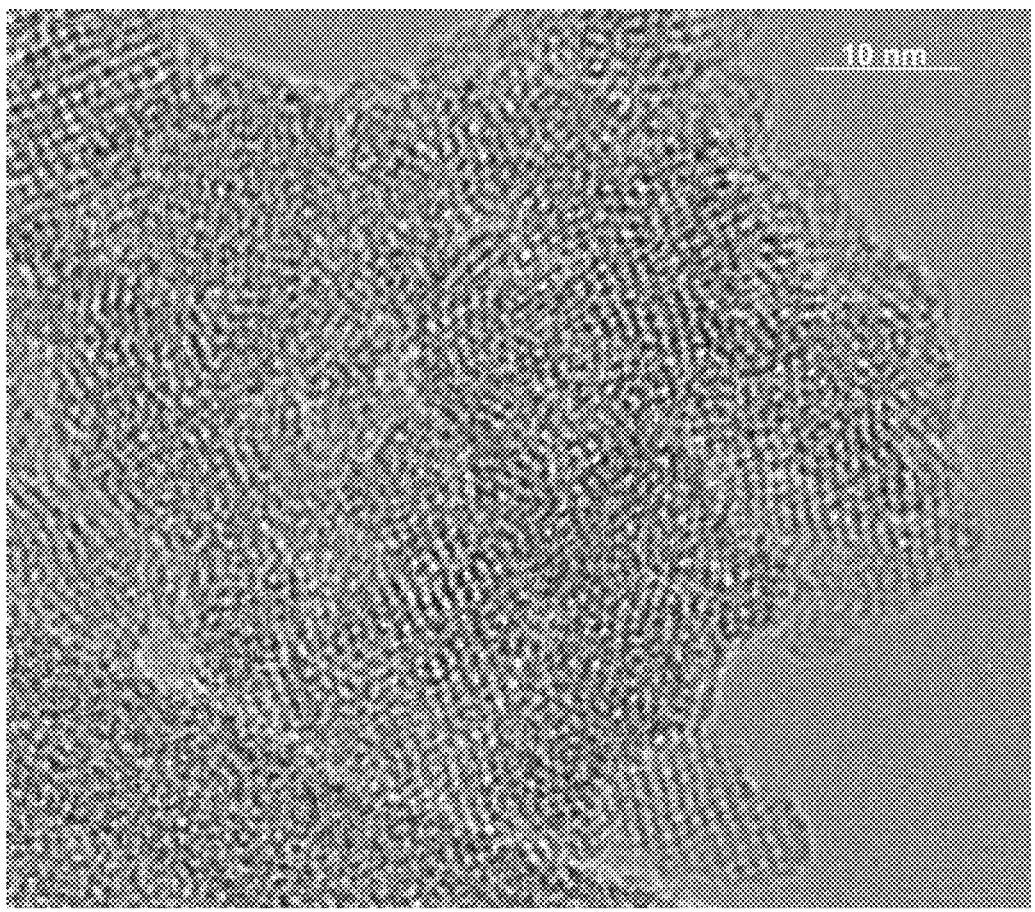
FIG. 5 shows a TEM micrograph of the Example 11 UZM-50 zeolite.
Figure 6:
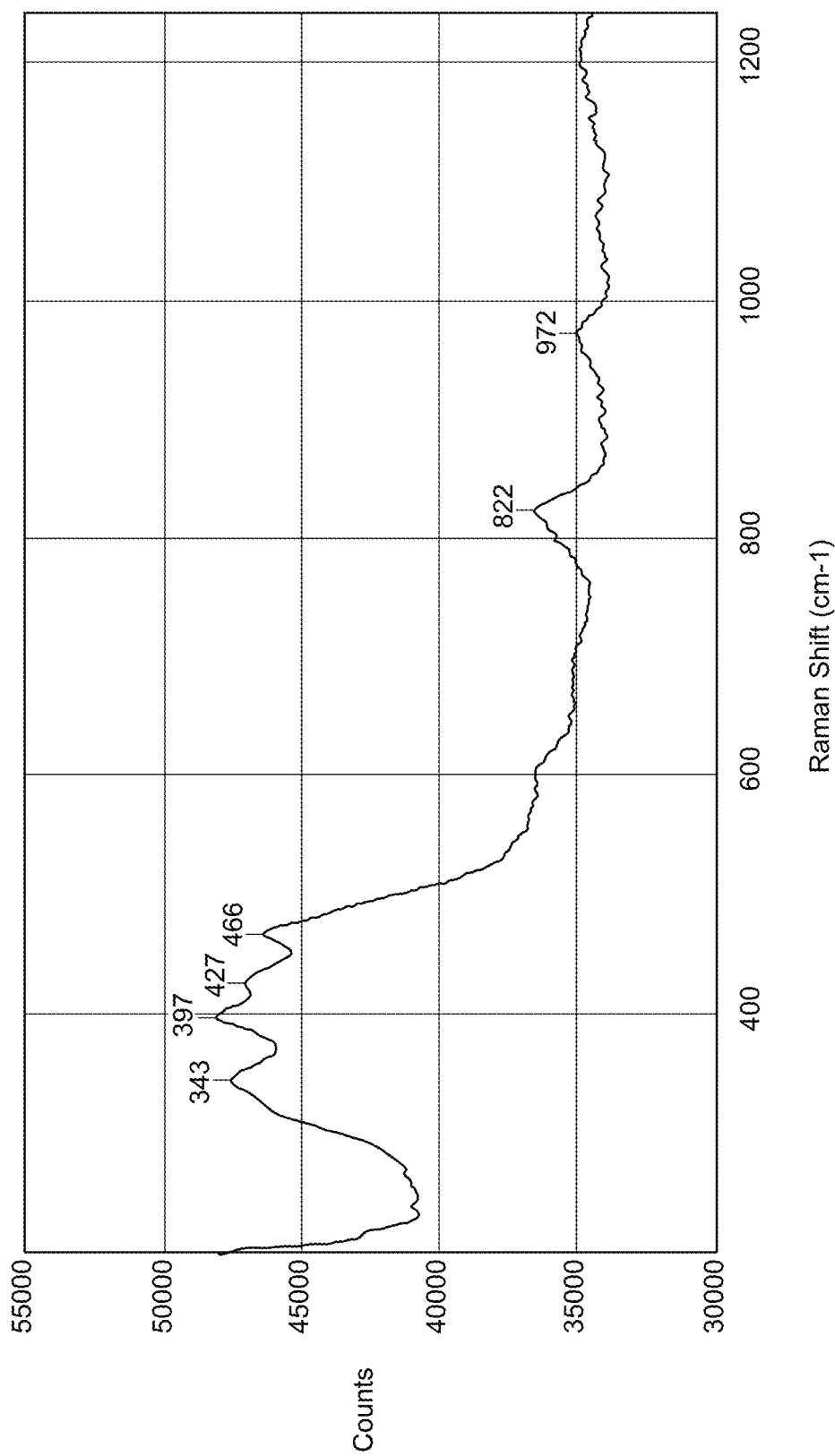
FIG. 6 shows the Raman spectrum of the Example 11 UZM-50 product.

3.24 g aluminum hydroxide (Aldrich) was stirred into 114.07 g Example 4 product. When it became a solution, 100 g Ludox AS-40 was added. To this mixture, 101.3 g deionized water was added, and the resulting mixture was placed in a 100° C. oven overnight in a sealed Teflon bottle. In the morning, this was found to be a soft gel. The gel was cooled, and 101.3 g water was added before the mixture was re-slurried for use. 211.55 g of this final mixture was divided equally among three 125 cc autoclaves and digested at 175° C. for 24 hours statically. UZM-50 was yielded from all three autoclaves. Materials were combined and then sampled for analysis. A portion was analyzed by TEM and shown to comprise very small crystallites as shown in FIG. 5. Significant faulting may be present. Elemental analyses showed the product to be 43.9% Si, 2.77% Al with a loss on ignition (LOI) of 26.7%, Si/Al=15.22, C/N=9.06, and N/Al=1.37. This material was then calcined at 600° for 6 hours under flowing air. A sample was analyzed by Raman and shown to have several peaks. The spectrum is shown in FIG. 6.

Analysis showed a Na BET SA of 644 $m^2/g$, Langmuir SA of 960 $m^2/g$, total pore volume of 1.307 mL/g, and micropore volume of 0.168 mL/g.

Example 12

1.08 g aluminum hydroxide (Aldrich) was stirred into 28.52 g Example 4 product. When it became a solution, 25 g Ludox AS-40 was added. This mixture was split evenly into Part A and Part B. 35.32 g water was added to the 27.3 g of the Part A mixture while stirring. This final mixture was evenly divided among two 45 cc autoclaves which were digested for 48 and 72 hours at 175° C. Meanwhile, 12.66 g water was added to the 27.3 g of the Part B mixture while stirring. This mixture was placed in a sealed Teflon bottle in a 100° C. oven for 18 hours. When cool, 12.66 g water was added to the gelatinous mixture, and it was re-slurried under a high speed Heidolph mixer. This final mixture was divided evenly among two 45 cc autoclaves which were digested for 48 and 72 hours at 175° C.

All four resulting products were centrifuged, washed, and dried. The products were identified as UZM-50 by XRD. There were no visible differences among the four from the XRD patterns. The two products from the 48 hour syntheses were sent for analysis. Results for Part A showed 44.4% Si, 3.26% Al with an LOI of 33.0%, Si/Al=13.08, C/N=9.08, and N/Al=0.96. This material was then calcined at 600° for 6 hours under flowing air. Analysis showed a $N_2$ BET SA of 668 $m^2/g$, Langmuir SA of 995 $m^2/g$, total pore volume of 1.521 mL/g, and micropore volume of 0.158 mL/g. Results for part B showed 43.1% Si, 3.22% Al with an LOI of 29.4%, Si/Al=12.86, C/N=9.03, and N/Al=1.01. This material was then calcined at 600° for 6 hours under flowing air. Analysis showed a $N_2$ BET SA of 674 $m^2/g$, Langmuir SA of 1004 $m^2/g$, total pore volume of 1.217 mL/g, and micropore volume of 0.162 mL/g. The materials were combined and ion-exchanged before analysis by SAXS in Example 32.

Example 13

Of $Al_2O_3 \cdot 3H_2O$ (gibbsite by XRD, 34.5% Al), 1.05 g was stirred into 47.64 g Example 4 product. To this slurry, 40 g Ludox AS-40 was added, followed by 83.4 g water. The final mixture was transferred to a 300 cc stirred autoclave. Synthesis was carried out at 175° C. for 40 hours while stirring at 250 rpm. The resulting product was identified as UZM-50 by XRD. Analysis showed 43.4% Si, 2.71% Al with an LOI of 26.8%, Si/Al=15.45, C/N=9.07, and N/Al=1.28.

Example 14

Of $Al_2O_3 \cdot 3H_2O$ (gibbsite by XRD, 34.5% Al), 8.4 g was stirred into 381.12 g Example 4 product. To this slurry, 320 g LudoxAS-40 was added, followed by 667.2 g water. The final mixture was transferred to a 2 L stirred autoclave. Stirring was started at 250 rpm, and the reactor was kept at 100° C. for 18 hours before digesting at 175° C. for 40 hours. The resulting product was identified as UZM-50 by XRD. Results showed 43.6% Si, 2.65% Al with an LOI of 24.2%, Si/Al=15.81, C/N=9.76, and N/Al=1.28. This material was then calcined at 600° for 6 hours under flowing AIR. Analysis showed a $N_2$ BET SA of 642 $m^2/g$, Langmuir SA of 949 $m^2/g$, total pore volume of 1.161 mL/g, and micropore volume of 0.174 mL/g. Another portion was calcined at 600° for 18 hours under flowing air. Analysis showed a $N_2$ BET SA of 622 $m^2/g$, Langmuir SA of 925 $m^2/g$, total pore volume of 1.582 mL/g, and micropore volume of 0.184 mL/g. A sample was calcined at 600° C. for 12 hours and then ion-exchange was then performed before the material was analyzed by SAXS in Example 32.

Example 15

Of $Al_2O_3 \cdot 3H_2O$ (gibbsite by XRD, 34.5% Al), 8.4 g was stirred into 364 g Example 3 product. To this slurry was added 320 g Ludox AS-40, followed by 667.2 g water. The final mixture was transferred to a 2 L stirred autoclave. Stirring was started at 250 rpm, and the reactor was kept at 100° C. for 18 hours before digesting at 160° C. for 120 hours. The resulting product was identified as UZM-50 by XRD. Results showed 44.5% Si, 2.73% Al with an LOI of 23.2%, Si/Al=15.66, C/N=6.2, and N/Al=1.16. This material was then calcined at 600° for 6 hours under flowing air. Analysis showed a $N_2$ BET SA of 623 $m^2/g$, Langmuir SA of 925 $m^2/g$, total pore volume of 0.999 mL/g, and micropore volume of 0.159 mL/g. Another portion was calcined at 600° for 18 hours under flowing air. Analysis shows a BET SA of 598 $m^2/g$, Langmuir SA of 889 $m^2/g$, total pore volume of 1.058 mL/g, and micropore volume of 0.163 mL/g.

Example 16

The example 6 mixture was loaded into 45 cc Parr bombs and digested statically. The product resulting from 125° C. digestion for 21 days was determined to be UZM-50 by XRD. The products resulting from 175° C. digestion for 1 and 3 days were determined to be UZM-50 by XRD. The product resulting from 175° C. digestion for 2 days was determined to be UZM-50 by XRD. Results showed 33.3% Si, 1.98% Al leading to a Si/Al=16.16. This material was calcined at 600° for 6 hours under flowing air. Analysis showed a $N_2$ BET SA of 659 $m^2/g$, Langmuir SA of 981 $m^2/g$, total pore volume of 1.416 mL/g, and micropore volume of 0.179 mL/g.

Example 17

Of $Al_2O_3 \cdot 3H_2O$, 8.4 g (gibbsite by XRD, 34.5% Al) was stirred into 381.12 g of the Example 4 product. To this slurry, 320 g Ludox AS-40 was then added, followed by 667.2 g water. The final mixture was transferred to a 2 L stirred autoclave. Synthesis was carried out at 175° C. for 40 hours while stirring at 250 rpm. The resulting product was identified as UZM-50 by XRD. Analysis showed 44.1% Si, 2.50% Al with an LOI of 23.2%, Si/Al=16.95, C/N=9.69, and N/Al=1.41. This material was calcined at 600° for 18 hours under flowing air. Analysis showed a Na BET SA of 600 $m^2/g$, Langmuir SA of 892 $m^2/g$, total pore volume of 1.410 mL/g, and micropore volume of 0.174 mL/g.

Example 18

Of $H_2O$, 413 g of water was weighed into a 2 L Teflon bottle. Of 1,5-dibromopentane, (97%, Aldrich) 474.1 g was added. To this mixture, 352 g Morpholine, 99% (Aldrich) was added. The Teflon bottle was moved into a 4 liter beaker as secondary containment and placed under a Heidolph mixer for stirring at room temperature (open system). Approximately 1-1.5 liters of cool water were added to the 4 liter beaker to disperse a strong exotherm should one occur. The exotherm was mild. After an hour, the result was a clear light orange "solution". The remaining 413 g water was mixed in. A sample was sent for $^{13}C$ NMR which showed that the desired spirocyclic compound resulted.

Example 19

Of DI $H_2O$, 437.8 g was weighed into a 2 L autoclave. Of 1,5-dibromopentane, (Aldrich, 97%) 237.05 g was added, followed by 204.34 g 4-methylmorpholine (Aldrich, 99%). Stirring was at 150 rpm while ramping to 69° C. The electronically controlled system "overshot" the target peaking at 76.8° C., yet maintained a level over 69° C. without having to call for heat from the reactor system for approximately 2.5 hours suggesting the reaction exotherm was able to sustain the temperature. After 6 hours at 77-69° C., heat was turned off while maintaining stirring as the reactor cooled to room temperature. Of unreacted 1,5-dibromopentane, 77 g was isolated and removed from the template solution. 360 g water was then added to the template solution.

Example 20

Of the Example 18 product, 1150 g was loaded into a 3-necked round bottom flask with overhead stirring. 336.4 g $Ag_2O$, 99% was added, and the flask was covered with aluminum foil. It was mixed for 48 hours at room temperature. Glass filters were used to isolate a clear yellowish solution. The solution was filtered a few times over the next week or two. Analysis showed the solution to be 64.6% water.

Example 21

Of the Example 19 product, 600 g was loaded into a 3-necked round bottom flask with overhead stirring. 164.1 g $Ag_2O$, 99% was added, and the flask was covered with aluminum foil. It was mixed for 48 hours at room temperature. Glass filters were used to isolate a clear yellow solution. The solution was filtered a few times over the next week or two. Analysis showed the solution to be 64.5% water.

Example 22

0.81 g aluminum hydroxide was weighed into a Teflon beaker, and 43.34 g of the example 21 product was added. When it became a solution, 25 g Ludox AS-40 was added. 44.62 g water was then added to the mixture while stirring. 1.67 g of a 10% NaOH solution was also added. This final mixture was evenly divided among five 45 cc autoclaves. An autoclave digested at 150° C. for 12 days yielded a product identified as UZM-50 by XRD. Analysis showed 44.8% Si, 2.72% Al with an LOI of 29.9%, Si/Al=15.82, C/N=9.37, N/Al=1.36, and Na/Al=0.11. This material was calcined at 600° C. for 4 hours under flowing air. Analysis showed a Na BET SA of 580 $m^2/g$, Langmuir SA of 862 $m^2/g$, total pore volume of 1.282 mL/g, and micropore volume of 0.173 mL/g.

Example 23

Of deionized $H_2O$, 355.57 g was weighed into a 2 L glass beaker. 355.57 g 1,5-dibromopentane, (Aldrich, 97%) was added, followed by 356.19 g 4-ethylmorpholine (Aldrich, 97%). The mixture was stirred on a hot plate with low heat. This was transferred to a 2 L Teflon bottle and put in a 100° oven overnight. The next morning, the solution was transferred to a 2 L autoclave and stirred on a hot plate at approximately 100° for 4 hours. Another 355.57 g water was then added.

Example 24

Of the example 23 product, 1257 g was loaded into a 3-necked round bottom flask with overhead stirring. 324.26 g $Ag_2O$, 99% was added, and the flask was covered with aluminum foil. It was mixed for 48 hours at room temperature. Glass filters were used to isolate a clear yellow solution. The solution was filtered a few times over the next week or two. Analysis showed the solution to be 65.9% water.

Example 25

2.02 g aluminum hydroxide was weighed into a Teflon beaker, and 72.76 g of the Example 24 product was added. When it became a solution, 25 g Ludox AS-40 was added. 26.60 g water was then added to the mixture while stirring. This final mixture was evenly divided among five 45 cc autoclaves. An autoclave digested at 135° for 18 days yielded a product identified as UZM-50 by XRD. Analysis showed 41.4% Si, 4.80% Al with an LOI of 25.5%, Si/Al=8.28, C/N=9.19, and N/Al=0.74. This material was calcined at 600° for 4 hours under flowing air. Analysis showed a $N_2$ BET SA of 689 $m^2/g$, Langmuir SA of 1032 $m^2/g$, total pore volume of 1.528 mL/g, and micropore volume of 0.151 mL/g.

Example 26

1.35 g aluminum hydroxide was weighed into a Teflon beaker, and 43.94 g of the Example 24 product was added. When it became a solution, 25 g Ludox AS-40 was added. 46.46 g water was then added to the mixture while stirring. 2.787 g of a 10% NaOH solution was also added. This final mixture was evenly divided among four 45 cc autoclaves. An autoclave digested at 135° for 11 days yielded a product identified as UZM-50 by XRD. This material was calcined at 600° for 12 hours under flowing air and ion-exchanged before analysis by SAXS in Example 32.

Example 27

9.71 g aluminum hydroxide was weighed into a Teflon beaker, and 480.78 g of the Example 21 product was added. When it became a solution, 300 g Ludox AS-40 was added. 614.92 g water was then added to the mixture while stirring. This final mixture was transferred to a 2 L stirred autoclave and digested at 135° C. for 14 days while stirring at 250 rpm. The resulting product was identified as UZM-50 by XRD. Analysis showed 43.2% Si, 3.39% Al with an LOI of 27.4%, Si/Al=12.74

Comparative Example 28

Zeolite beta was acquired from Clariant at Si/Al=75 as CZB 150 and extruded as 1/16" cylinders of 70/30 beta/$Al_2O_3$ composition and calcined at 550° C. for 3 hours in air.

Comparative Example 29

Zeolite beta was acquired from Clariant at Si/Al=12.5 as CZB 25 and extruded as 1/16" cylinders of 70/30 beta/$Al_2O_3$ composition and calcined at 550° C. for 3 hours in air.

Example 30

The product from Example 14 after calcination at 600° C. was extruded as 1/16" cylinders of 70/30 UZM-50/$Al_2O_3$ composition and calcined at 550° C. for 3 hours in air.

Example 31

The extruded catalysts of Examples 28-30 were used for the conversion of ethylbenzene. Testing was carried out at 10WHSV. Conversion, pX/X and xylene loss were determined at 260° C., 280° C. and 300° C. The feed comprised 0.9 wt % p-xylene, 64.9 wt % m-xylene, 29.7 wt % o-xylene and 4.3 wt % ethylbenzene. As pX/X is the percentage of p-xylene in the total amount of xylene (ethylbenzene is not a xylene), the pX/X of the feed was 0.94. Equilibrium at these temperatures is about 24. Xylene loss was calculated by summing the total amount of xylenes in the feed and in the product and using the equation $$XL=100-(Xyl_{prod}/Xyl_{feed})*100$$

Figure 7:
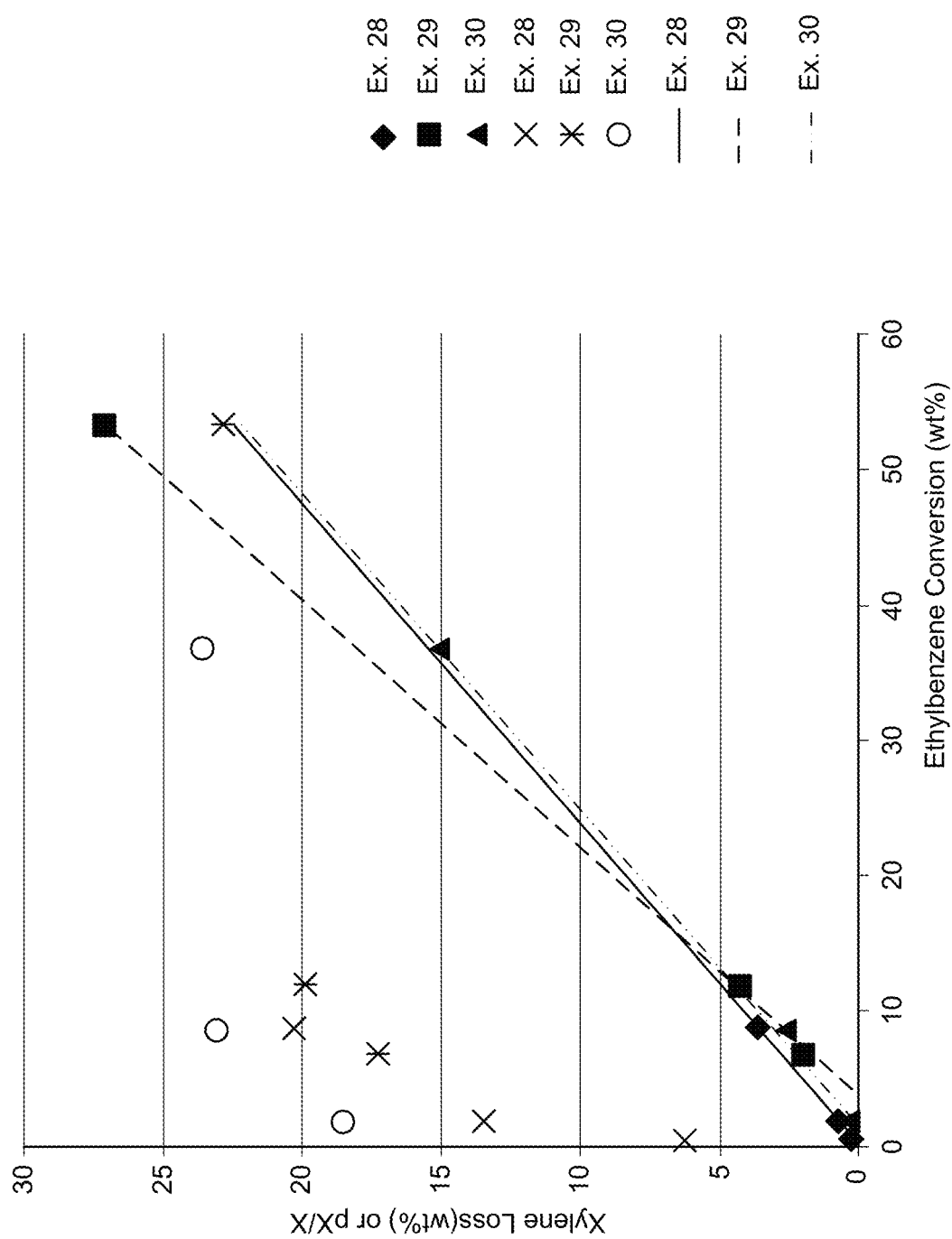
FIG. 7 shows a comparison of ethylbenzene conversion as a function of xylene loss and pX/X for UZM-50 and beta zeolite.

Results obtained from the experiment are reported in Table 4 and in the graph shown as FIG. 7.

TABLE 4

| Catalyst | Example 28 | Example 29 | Example 30 |
|---|---|---|---|
| Conversion 260° C. | 0.45 | 6.88 | 1.88 |
| Conversion 280° C. | 1.8 | 11.98 | 8.63 |
| Conversion 300° C. | 8.76 | 53.38 | 36.91 |
| Xylene Loss 260° C. | 0.12 | 1.98 | 0.41 |
| Xylene Loss 280° C. | 0.54 | 4.21 | 2.63 |
| Xylene Loss 300° C. | 3.59 | 27.14 | 15.23 |
| pX/X 260° C. | 6.26 | 17.31 | 18.51 |
| pX/X 280° C. | 13.47 | 19.92 | 23.08 |
| pX/X 300° C. | 20.32 | 22.87 | 23.6 |

Xylene loss increased as ethylbenzene conversion increased; the UZM-50 catalyst of Example 30 (triangles) and the CZB 150 catalyst of Example 28 (diamonds) were on the same xylene loss/ethylbenzene conversion curve as shown by the nearly identical linear fits for these two catalysts (Ex 30 solid fit, Ex 28 hashed fit), whereas the CZB 75 catalyst of Example 29 had much higher xylene loss per unit of ethylbenzene conversion (dashed fit). The example 30 UZM-50 catalyst has the highest pX/X ratio as a function of ethylbenzene conversion (circles) of the catalysts, whereas the Example 28 (x markers) and Example 29 (Greek crosses) catalysts exhibited lower ratios. Therefore, the best catalyst was the UZM-50 catalyst of Example 30 as it combined both beneficial properties.

Example 32 SAXS Fitting of UZM-50 and Beta Zeolite Samples

Small Angle X-ray Scattering (SAXS) is an x-ray based technique which may be used to study and quantify features from 1-100 nm in size. The SAXS experiment probes electron density contrast in a material and as a result, scattering features can arise from a variety of sources including particles, pore structures or density differences in single-phase samples. SAXS profiles were obtained on a RIGAKU SMARTLAB® system operating in transmission mode with a line collimation setup. The SmartLab's rotating anode power makes the measurement extremely sensitive, allowing measurement of dilute or weakly contrasting scatterers. NANO-Solver® provides size distribution functions of nanoscale pore/particles and correlation length functions for materials with density fluctuation based on the non-linear least square curve fitting analysis of X-ray small angle scattering profiles.

Powdered samples were prepared and held between 2 layers of polypropylene film mounted on the Rigaku transmission SAXS sample stage, background correction was performed prior to sample measurements with only 2 layers of the same polypropylene film (0.00025" thickness). The low angle scattering data were collected from 20 values of 0.12 to 6 degrees with a Cu K-α X-ray beam of wavelength 1.54 Å. The X-rays were generated at 45 kv and 200 mA by rotating anode source for improved intensity. Typical data collection times were on the order of 30 mins. The raw scattering data was analyzed using Rigaku's NANO-SOLVER® software using a split interval of 50 with high slit correction factor.

Figure 8:
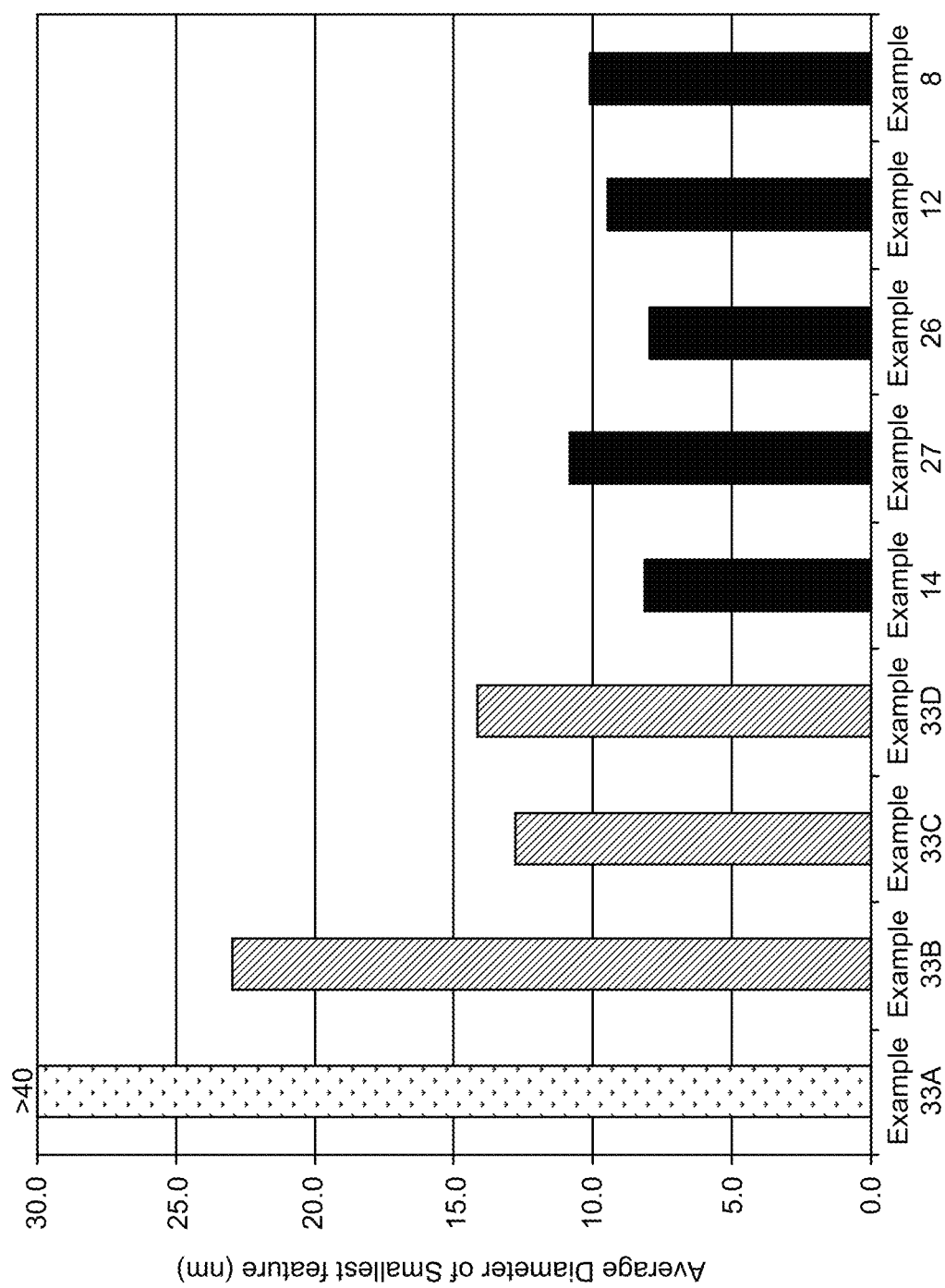
FIG. 8 compares the average diameter of the smallest features observed by SAXS for UZM-50 and beta zeolite.

The data fitted using NANO-Solver® assumed a density contrast between silica or silica/alumina framework (i.e. the crystals) and pore/air. For these samples of interest, all UZM-50 samples required a minimum of 2 distinct size features to fit the observed data. Without wishing to be bound by theory, it is believed that in the UZM-50 samples analyzed here, the smallest size feature observed is due to the crystallite size of the primary UZM-50 crystals. Comparative samples of various beta zeolite preparations were also analyzed. One larger feature was observed >25 nm and a distinct smaller scattering feature consistently in the 6 nm-12 nm size range. The size of the smaller feature fitted for each sample is plotted in FIG. 8 and shown numerically in Table 5.

Unless otherwise noted, materials were analyzed following calcination at 600° C. for 12 hours and ion-exchange with $NH_4NO_3$ followed by calcination at 500° C. to yield $H^+$ form materials.

TABLE 5

| Sample | Feature A (Å) | Feature B (Å) |
|---|---|---|
| Example 33A | >40 | Not detected* |
| Example 33B | 23.0 | Not detected* |
| Example 33C | 12.8 | 76.0 |
| Example 33D | 14.1 | 85.3 |
| Example 14 | 8.11 | 30.5 |
| Example 27 | 10.8 | 46.1 |
| Example 26 | 7.89 | 29.4 |
| Example 12 | 9.45 | 32.9 |
| Example 8 | 10.0 | 35.2 |

*Data sets can be modelled by a single feature

Comparative Example 33

A number of beta zeolite samples were acquired from vendors. Zeolyst supplied a sample of CP814Q, a material with a $SiO_2/Al_2O_3$=50, hereinafter Example 33A. Zeolyst also supplied a sample of CP811E, a material with $SiO_2/Al_2O_3$=75, hereinafter Example 33B. Zeolyst also supplied a sample of CP811E-150, a material with $SiO_2/Al_2O_3$=150, hereinafter Example 33C. We also acquired a sample of an acid washed beta prepared by a toll manufacturer according to the methods of U.S. Pat. No. 6,162,416. This material had a $SiO_2/Al_2O_3$=25.3, hereinafter Example 33D.

Example 34

196.5 g deionized water was weighed into a 2 L autoclave. 254.14 g 1,6-dibromohexane, 96% was added, followed by 204.34 g 4-methylmorpholine, 99%. The autoclave was placed in an oven at 125° overnight. When cooled the following morning, there was brown liquid with some clear unreacted liquid and crystalline solid material on the bottom. 261.9 g deionized water was added. The autoclave was placed back into the 125° oven overnight. A brown liquid with no solids resulted.

Example 35

A portion of the Example 34 solution was loaded into a 3-necked round bottom flask with overhead stirring. $Ag_2O$, 99% was added, and the flask was covered with aluminum foil. It was mixed for 48 hours at room temperature. Glass filters were used to isolate a clear yellow solution. The solution was filtered a few times over the next week or two. Analysis showed the solution to be 60.9% water.

Example 36

0.81 g aluminum hydroxide was weighed into a Teflon beaker, and 41.15 g 1,6-bis(4-Methylmorpholinium)hexane dihydroxide, 39.1% was added. When it became a solution, 25 g. Ludox AS-40 was added. 52.08 g water was then added to the mixture while stirring. This final mixture was evenly divided among five 45 cc autoclaves. A resulting product which was digested at 160° C. for 5 days statically was identified as UZM-50 by XRD.

Example 37

333.37 g deionized water was weighed into a 2 L Teflon bottle. 327.14 g 1,4-dibromobutane, 99% was added, followed by 339.6 g 4-Ethylpiperidine, 97%. The mixture was placed in a 4 L metal beaker with water between the Teflon bottle and beaker and stirred on a hot plate with low heat. Another 333.37 g water was later stirred in. 18.2 g of unreacted dibromobutane was removed by separation funnel.

Example 38

1200 g of the Example 37 solution was loaded into a 3-necked round bottom flask with overhead stirring. 322.2 g $Ag_2O$, 99% was added, and the flask was covered with aluminum foil. It was mixed for 48 hours at room temperature. Glass filters were used to isolate a clear yellow solution. The solution was filtered a few times over the next week or two. Analysis showed the solution to be 66.3% water.

Example 39

0.16 g aluminum hydroxide was weighed into a Teflon beaker, and 47.17 g of the Example 38 solution was added. When it became a solution, 25 g Ludox AS-40 was added. 66.79 g. water was then added to the mixture while stirring. This final mixture was evenly divided among five 45 cc autoclaves. A resulting product which was digested at 135° for 21 days statically was identified as UZM-50 by XRD.

Comparative Example 40

A number of zeolite samples of various structure types were acquired from vendors. Zeolyst supplied a sample of MTT zeolite as product ZD2K019E. This material was extruded with alumina at a 25% zeolite content and calcined at 550° C. for 3 hours in air, hereinafter Example 40A. Zeolyst supplied a sample of MFI zeolite as MFI-23, a zeolite with $SiO_2/Al_2O_3$=23. This material was extruded with alumina at a 70% zeolite content and calcined at 550° C. for 3 hours in air, hereinafter Example 40B. Zeolyst also supplied a sample of MFI zeolite as MFI-40, a zeolite with $SiO_2/Al_2O_3$=40. This material was extruded with alumina at a 70% zeolite content and calcined at 550° C. for 3 hours in air, hereinafter Example 40C. A sample of UZM-44 was synthesized according to the methods of U.S. Pat. No. 8,623,321. This material was extruded with alumina at a 70% zeolite content and calcined at 550° C. for 3 hours in air, hereinafter Example 40D. A high IMF sample of UZM-39 was synthesized according to the methods of U.S. Pat. No. 8,992,885. This material was extruded with alumina at a 70% zeolite content and calcined at 550° C. for 3 hours in air, hereinafter Example 40E.

Example 41 Constraint Index Testing

Constraint Index (CI) is a test describing the relative propensity of a material to crack linear alkanes versus branched alkanes. The competitive cracking of n-hexane versus 3-methylpentane was first described by Haag and coworkers *J. Catal.* 1981, 67, 218. Additional work to help clarify results of the test have been performed by Zones and Harris *Micro. Meso. Mater.* 2000, 35-6, 31-36 and Davis and coworkers *J. Catal.* 2010, 269, 64-70. The CI value may be calculated using Eq. (1) (X denotes the fractional conversion of each species) and thus it is proportional to the observed cracking rate constants of n-hexane (nC6) to 3-methylpentane (3MP).

$$CI = \frac{\log(1 - XnC6)}{\log(1 - X3MP)} \qquad \text{Equation 1}$$

The UZM-50 catalyst of example 30 was characterized via constraint index testing. Several comparative materials were also tested. Of each catalyst, 5 mL comprising between 2.5 and 3.5 g was loaded into a steel reactor. Conditions were as follows: 5 psig; LHSV=1; liquid feed rate=5 mL/hr; He flow 86 sccm; (HC/He=1:4) using a feed of 50/50 n-hexane/3-methylpentane. Temperatures needed to achieve an overall conversion between 10% and 50% varied from about 420° C. (Example 30 catalyst) to 396° C. (Example 40A catalyst) to between 280 and 300° C. (Examples 40B, 40C, 40D, 40E catalyst) to 267° C. (Example 29 catalyst). Cracked products including propylene were observed from the conversion of hexanes.

As is typically reported, catalysts comprising 8-membered ring pores or small 10-membered-ring zeolite structures such as MTT (example 40A) exhibit CI values greater than 12. Catalysts comprising 10-membered pores of a slightly larger diameter and often with a 3-dimensional pore architecture such as MFI, TUN, IMF, (examples 40B, 40C, 40D, 40E) often exhibit CI values in the range from about 2 to about 12. Large pore zeolites, such as the three-dimensional 12-membered ring pore system of BEA* (Example 29) usually exhibit CI values of less than 1. The UZM-50 catalyst of Example 30 exhibits a CI value of about 1.5. In an embodiment, UZM-50 may have a CI value of from 1 to about 3. In an aspect, the CI value may be greater than 1, or greater than 1.1, or greater than 1.2, or greater than 1.25, or greater than 1.3. In an aspect, the CI value may be less than 3, or less than 2.5, or less than 2, or less than 1.9, or less than 1.8, or less than 1.75.

TABLE 6

| Catalyst | CI value |
| --- | --- |
| Example 29 | 0.25 ± 0.24 |
| UZM-50 | 1.50 ± 0.06 |
| Example 40E | 2.5 ± 0.4 |
| Example 40D | 3.4 ± 0.8 |
| Example 40B | 5.3 ± 1.5 |
| Example 40C | 8.8 ± 5.5 |
| Example 40A | 16.9 ± 5.6 |

TABLE 6-continued

| Catalyst | CI value |
|---|---|

While at least one exemplary embodiment has been presented in the foregoing detailed description of the invention, it should be appreciated that a vast number of variations exist.

It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a hydrocarbon conversion process comprising contacting a hydrocarbon stream with a catalyst at hydrocarbon conversion conditions to give a converted product, the catalyst comprising a microporous crystalline zeolite having a three-dimensional framework of at least $AlO_2$ and $SiO_2$ tetrahedral units and a composition in an as synthesized and anhydrous basis expressed by an empirical formula of $$M^+{}_m R_r Al_{1-x} E_x Si_y O_z$$

where M is selected from the group consisting of hydrogen, sodium, potassium, magnesium, calcium, and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of N from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation $z=(m+3+4 \cdot y)/2$, and is characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table A:

TABLE A

| 2θ | d (Å) | I/I$_0$ % |
|---|---|---|
| ~7.5 | 11.5-11.9 | S |
| ~22.4 | 3.92-3.99 | VS | or a microporous crystalline zeolite having a three-dimensional framework of at least $AlO_2$ and $SiO_2$ tetrahedral units and a composition in an after calcination and on an anhydrous basis expressed by an empirical formula of $$M1^+{}_{m1} Al_{1-x} E_x Si_y O_z$$

where M1 represents hydrogen, sodium, potassium, magnesium, calcium, ammonium, hydrogen, or combinations thereof, "m1" is the mole ratio of M to (Al+E) and varies from 0 to about 1, and E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation $z=(m+3+4 \cdot y)/2$, and is characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table B:

TABLE B

| 2θ | d (Å) | I/I$_0$ % |
|---|---|---|
| ~7.5 | 11.5-11.9 | VS |
| ~22.4 | 3.93-3.98 | VS |

An embodiment of the invention is one, any or all of prior embodiments in this paragraph up through the first embodiment in this paragraph wherein there are no more than three peaks of at least strong intensity in the x-ray diffraction pattern. An embodiment of the invention is one, any or all of prior embodiments in this paragraph up through the first embodiment in this paragraph wherein there are no more than two peaks of at least strong intensity in the x-ray diffraction pattern. An embodiment of the invention is one, any or all of prior embodiments in this paragraph up through the first embodiment in this paragraph wherein the catalyst has an InterPeak distance of greater than 14.75°2θ and less than 15.25°2θ as determined using Cu x-rays of 1.5418 Å wavelength. An embodiment of the invention is one, any or all of prior embodiments in this paragraph up through the first embodiment in this paragraph wherein the catalyst has a Peak 1 FWHM of greater than about 1.25°2θ and less than 2.00°2θ as determined using Cu x-rays of 1.5418 Å wavelength. An embodiment of the invention is one, any or all of prior embodiments in this paragraph up through the first embodiment in this paragraph wherein the catalyst has a CI value in a range of 1 to 3. An embodiment of the invention is one, any or all of prior embodiments in this paragraph up through the first embodiment in this paragraph wherein x has a value of from 0 to 0.5, and y has a value from 6 to 50. An embodiment of the invention is one, any or all of prior embodiments in this paragraph up through the first embodiment in this paragraph wherein the average diameter of the smallest feature observed by SAXS is less than 11 nm. An embodiment of the invention is one, any or all of prior embodiments in this paragraph up through the first embodiment in this paragraph wherein the average diameter of the smallest feature observed by SAXS is less than 10 nm. An embodiment of the invention is one, any or all of prior embodiments in this paragraph up through the first embodiment in this paragraph wherein the catalyst has a $N_2$ micropore volume of about 0.14 to about 0.2 mL/g. An embodiment of the invention is one, any or all of prior embodiments in this paragraph up through the first embodiment in this paragraph wherein the ratio of the $N_2$ mesopore volume to total pore volume≥0.88. An embodiment of the invention is one, any or all of prior embodiments in this paragraph up through the first embodiment in this paragraph wherein the hydrocarbon conversion process is selected from the group consisting of oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

A second embodiment of the invention is a hydrocarbon conversion process comprising contacting a hydrocarbon stream with a catalyst at hydrocarbon conversion conditions to give a converted product, the catalyst comprising a microporous crystalline zeolite having a three-dimensional framework of at least $AlO_2$ and $SiO_2$ tetrahedral units and a composition in an as synthesized and anhydrous basis expressed by an empirical formula of

$$M^+_m R_r Al_{1-x} E_x Si_y O_z$$

where M is selected from the group consisting of hydrogen, sodium, potassium, magnesium, calcium, and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of N from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation $z=(m+3+4\cdot y)/2$, and is characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table A and there are no more than two peaks of at least strong intensity in the x-ray diffraction pattern:

TABLE A

| 2θ | d (Å) | I/I₀ % |
|---|---|---|
| ~7.5 | 11.5-11.9 | S |
| ~22.4 | 3.92-3.99 | VS | or a microporous crystalline zeolite having a three-dimensional framework of at least $AlO_2$ and $SiO_2$ tetrahedral units and a composition in an after calcination and on an anhydrous basis expressed by an empirical formula of

$$M1^+_{m1} Al_{1-x} E_x Si_y O_z$$

where M1 represents hydrogen, sodium, potassium, magnesium, calcium, ammonium, hydrogen, or combinations thereof, "m1" is the mole ratio of M to (Al+E) and varies from 0 to about 1, and E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation $z=(m+3+4\cdot y)/2$, and is characterized in that an average diameter of the smallest feature observed by SAXS is less than 12 nm, it has a ratio of a $N_2$ mesopore volume to total pore volume≥0.85, and it has the x-ray diffraction pattern having at least the d-spacing's and intensities set forth in Table B and there are no more than two peaks of at least strong intensity in the x-ray diffraction pattern:

TABLE B

| 2θ | d (Å) | I/I₀ % |
|---|---|---|
| ~7.5 | 11.5-11.9 | VS |
| ~22.4 | 3.93-3.98 | VS |

An embodiment of the invention is one, any or all of prior embodiments in this paragraph up through the second embodiment in this paragraph wherein the catalyst has an InterPeak distance of greater than 14.75°2θ and less than 15.25°2θ as determined using Cu x-rays of 1.5418 Å wavelength. An embodiment of the invention is one, any or all of prior embodiments in this paragraph up through the second embodiment in this paragraph wherein the catalyst has a CI value in a range of 1 to 3. An embodiment of the invention is one, any or all of prior embodiments in this paragraph up through the second embodiment in this paragraph wherein x has a value of from 0 to 0.5, and y has a value from 6 to 50. An embodiment of the invention is one, any or all of prior embodiments in this paragraph up through the second embodiment in this paragraph wherein the average diameter of the smallest feature observed by SAXS is less than 10 nm. An embodiment of the invention is one, any or all of prior embodiments in this paragraph up through the second embodiment in this paragraph wherein the catalyst has a $N_2$ micropore volume of about 0.14 to about 0.2 mL/g. An embodiment of the invention is one, any or all of prior embodiments in this paragraph up through the second embodiment in this paragraph wherein the ratio of the $N_2$ mesopore volume to total pore volume≥0.88. An embodiment of the invention is one, any or all of prior embodiments in this paragraph up through the second embodiment in this paragraph wherein the hydrocarbon conversion process is selected from the group consisting of oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A hydrocarbon conversion process comprising contacting a hydrocarbon stream with a catalyst at hydrocarbon conversion conditions to give a converted product, the catalyst comprising a microporous crystalline zeolite having a three-dimensional framework of at least $AlO_2$ and $SiO_2$ tetrahedral units and a composition in an as synthesized and anhydrous basis expressed by an empirical formula of:

$$M^+{}_mR_rAl_{1-x}E_xSi_yO_z$$

where M is selected from the group consisting of hydrogen, sodium, potassium, magnesium, calcium, and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of N from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4·y)/2$, and is characterized in that an average diameter of the smallest feature observed by SAXS is less than 12 nm, it has a ratio of a $N_2$ mesopore volume to total pore volume ≥0.88, it has a $N_2$ micropore volume of about 0.14 to about 0.2 mL/g and it has the x-ray diffraction pattern having at least the d-spacing's and intensities set forth in Table A:

TABLE A

| 2θ | d(Å) | I/I₀ % |
|---|---|---|
| ~7.5 | 11.5-11.9 | S |
| ~22.4 | 3.92-3.99 | VS | or
a microporous crystalline zeolite having a three-dimensional framework of at least $AlO_2$ and $SiO_2$ tetrahedral units and a composition in an after calcination and on an anhydrous basis expressed by an empirical formula of:

$$M1^+{}_{m1}Al_{1-x}E_xSi_yO_z$$

where M1 represents hydrogen, sodium, potassium, magnesium, calcium, ammonium, hydrogen, or combinations thereof, "m1" is the mole ratio of M to (Al+E) and varies from 0 to about 1, and E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4·y)/2$, and is characterized in that an average diameter of the smallest feature observed by SAXS is less than 12 nm, it has a ratio of a $N_2$ mesopore volume to total pore volume ≥0.88, it has a $N_2$ micropore volume of about 0.14 to about 0.2 mL/g and it has the x-ray diffraction pattern having at least the d-spacing's and intensities set forth in Table B:

TABLE B

| 2θ | d (Å) | I/I₀ % |
|---|---|---|
| ~7.5 | 11.5-11.9 | VS |
| ~22.4 | 3.93-3.98 | VS. |

2. The process of claim 1 wherein there are no more than three peaks of at least strong intensity in the x-ray diffraction pattern.

3. The process of claim 1 wherein there are no more than two peaks of at least strong intensity in the x-ray diffraction pattern.

4. The process of claim 1 wherein the catalyst has an InterPeak distance of greater than 14.75° 2θ and less than 15.25° 2θ as determined using Cu x-rays of 1.5418 Å wavelength.

5. The process of claim 1 wherein the catalyst has a Peak 1 FWHM of greater than about 1.25° 2θ and less than 2.00020 as determined using Cu x-rays of 1.5418 Å wavelength.

6. The process of claim 1 wherein the catalyst has a CI value in a range of 1 to 3.

7. The process of claim 1 wherein x has a value of from 0 to 0.5, and y has a value from 6 to 50.

8. The process of claim 1 wherein the average diameter of the smallest feature observed by SAXS is less than 11 nm.

9. The process of claim 1 wherein the average diameter of the smallest feature observed by SAXS is less than 10 nm.

10. The process of claim 1 wherein the hydrocarbon conversion process is selected from the group consisting of oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

11. A hydrocarbon conversion process comprising contacting a hydrocarbon stream with a catalyst at hydrocarbon conversion conditions to give a converted product, the catalyst comprising a microporous crystalline zeolite having a three-dimensional framework of at least $AlO_2$ and $SiO_2$ tetrahedral units and a composition in an as synthesized and anhydrous basis expressed by an empirical formula of:

$$M^+{}_mR_rAl_{1-x}E_xSi_yO_z$$

where M is selected from the group consisting of hydrogen, sodium, potassium, magnesium, calcium, and combinations thereof, "m" is the mole ratio of M to (Al+E) and varies from 0 to about 1, R is the organic structure directing agent or agents derived from reactants R1 and R2 where R1 is an amine essentially incapable of undergoing pyramidal inversion and having 7 or fewer carbon atoms, and R2 is a dihaloalkane, "r" is the mole ratio of N from the organic structure directing agent or agents to (Al+E) and has a value of from about 0.2 to about 4, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4·y)/2$, and is characterized in that an average diameter of the smallest feature observed by SAXS is less than 12 nm, it has a ratio of a $N_2$ mesopore volume to total pore volume≥0.88, it has a $N_2$ micropore volume of about 0.14 to about 0.2 mL/g and it has the x-ray diffraction pattern having at least the d-spacing's and intensities set forth in Table A and there are no more than two peaks of at least strong intensity in the x-ray diffraction pattern:

TABLE A

| 2θ | d (Å) | $I/I_0$ % |
|---|---|---|
| ~7.5 | 11.5-11.9 | S |
| ~22.4 | 3.92-3.99 | VS | or
a microporous crystalline zeolite having a three-dimensional framework of at least $AlO_2$ and $SiO_2$ tetrahedral units and a composition in an after calcination and on an anhydrous basis expressed by an empirical formula of:

$$M1^+_{m1}Al_{1-x}E_xSi_yO_z$$

where M1 represents hydrogen, sodium, potassium, magnesium, calcium, ammonium, hydrogen, or combinations thereof, "m1" is the mole ratio of M to (Al+E) and varies from 0 to about 1, and E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 60 and "z" is the mole ratio of O to (Al+E) and has a value determined by the equation: $z=(m+3+4\cdot y)/2$, and is characterized in that an average diameter of the smallest feature observed by SAXS is less than 12 nm, it has a ratio of a $N_2$ mesopore volume to total pore volume≥0.88, it has a $N_2$ micropore volume of about 0.14 to about 0.2 mL/g and it has the x-ray diffraction pattern having at least the d-spacing's and intensities set forth in Table B and there are no more than two peaks of at least strong intensity in the x-ray diffraction pattern:

TABLE B

| 2θ | d (Å) | $I/I_0$ % |
|---|---|---|
| ~7.5 | 11.5-11.9 | VS |
| ~22.4 | 3.93-3.98 | VS. |

12. The process of claim 11 wherein the catalyst has an InterPeak distance of greater than 14.75° 2θ and less than 15.25° 2θ as determined using Cu x-rays of 1.5418 Å wavelength.

13. The process of claim 11 wherein the catalyst has a CI value in a range of 1 to 3.

14. The process of claim 11 wherein x has a value of from 0 to 0.5, and y has a value from 6 to 50.

15. The process of claim 11 wherein the average diameter of the smallest feature observed by SAXS is less than 10 nm.

16. The process of claim 11 wherein the hydrocarbon conversion process is selected from the group consisting of oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

* * * * *